(12) United States Patent
Shukla et al.

(10) Patent No.: US 9,464,113 B2
(45) Date of Patent: Oct. 11, 2016

(54) ANTI-HEPARAN SULFATE PEPTIDES THAT BLOCK HERPES SIMPLEX VIRUS INFECTION IN VIVO

(71) Applicant: The Board of Trustees of the University of Illinois, Urbana, IL (US)

(72) Inventors: Deepak Shukla, Orland Park, IL (US); Vaibhav Tiwari, Downers Grove, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 92 days.

(21) Appl. No.: 14/555,000

(22) Filed: Nov. 26, 2014

(65) Prior Publication Data

US 2015/0093825 A1 Apr. 2, 2015

Related U.S. Application Data

(60) Division of application No. 13/842,193, filed on Mar. 15, 2013, now abandoned, which is a continuation-in-part of application No. PCT/US2011/052002, filed on Sep. 16, 2011.

(60) Provisional application No. 61/383,520, filed on Sep. 16, 2010, provisional application No. 61/651,643, filed on May 25, 2012.

(51) Int. Cl.
  *C07K 7/08* (2006.01)
  *C07K 7/06* (2006.01)
  *A61K 47/48* (2006.01)

(52) U.S. Cl.
  CPC .............. *C07K 7/08* (2013.01); *A61K 47/4833* (2013.01); *C07K 7/06* (2013.01)

(58) Field of Classification Search
  CPC ....................................................... C07K 7/08
  See application file for complete search history.

(56) References Cited

U.S. PATENT DOCUMENTS

| | | |
|---|---|---|
| 5,166,173 A | 11/1992 | Hwang et al. |
| 2002/0119165 A1 | 8/2002 | Lambris et al. |
| 2006/0051368 A1 | 3/2006 | Spear et al. |
| 2006/0172941 A1 | 8/2006 | Rastelli et al. |
| 2009/0068215 A1 | 3/2009 | Davido et al. |
| 2009/0203043 A1 | 8/2009 | Hornbeck et al. |

FOREIGN PATENT DOCUMENTS

WO 03/093434 11/2003

OTHER PUBLICATIONS

Park, Paul J. et al., "An Investigative Peptide-Acyclovir Combination to Control Herpes Simplex Virus Type 1 Ocular Infection," Investigative Ophthalmology & Visual Science, Sep. 2013, vol. 54, pp. 6373-6381.
International Search Report & Written Opinion, issued in PCT Application No. PCT/US2011/052002, mailed May 21, 2012, 13 pages.
International Preliminary Report on Patentability, issued in PCT Application No. PCT/US2011/052002, mailed Mar. 19, 2013, 7 pages.
Tiwari, V. et al., "Anti-heparan Sulfate Peptides that Block Herpes Simplex Virus Infection in Vivo," J. Bio. Chem., Jul. 15, 2011, pp. 25406-25415, vol. 286, No. 28.
European Search Report, issued in European Patent Application No. 11826047.0, mailed Mar. 21, 2014, 5 pages.
Trybala, E. et al., "Structural and functional features of the polycationic peptide required for inhibition of herpes simplex virus invasion of cells," Antiviral Research, 2004, pp. 125-134, vol. 62.
Kim, H. H. et al., "Basic peptide system for efficient delivery of foreign genes," Biochimica et Biophysica Acta, 2003, pp. 129-136, vol. 1640.
Curtis, Bruce A. et al., "Algal Genomes Reveal Evolutionary Mosaicism and the Fate of Nucleomorphs," Ntauare, 2012, vol. 492, pp. 59-65.

*Primary Examiner* — Amber D Steele
(74) *Attorney, Agent, or Firm* — Schwabe Williamson & Wyatt

(57) ABSTRACT

Provided are anti-heparan sulfate peptides and methods that employ those peptides for the prevention or treatment of viral infections, including herpesviral infections such as α-herpesviral, β-herpesviral, and γ-herpesviral infections, which are exemplified by HSV-1. CMV, and HHV-8 viral infections, respectively. Peptides may comprise at least 10 amino acids of the amino acid sequences

XRXRXKXXRXRX,     (SEQ ID NO: 2)

XRXRXXKXRXRX,    (SEQ ID NO: 8)

XXRRRRXRRRXK,    (SEQ ID NO: 4)
and/or

KXRRRXRRRXX,     (SEQ ID NO: 10)

wherein X represents any amino acid. In some embodiments, peptides comprise at least 10 amino acids of the sequence LRSRTKIIRIRH (SEQ ID NO: 1), HRIRIIK-TRSRL (SEQ ID NO: 7), MPRRRRIRRRQK (SEQ ID NO: 3), and/or KQRRRIRRRRM (SEQ ID NO: 9). Peptides may be coupled to one or more therapeutic compound(s) to generate peptide-therapeutic compound conjugates, wherein the therapeutic compound may be one or more of a nucleoside analog, an oligosaccharide, and a small molecule.

20 Claims, 8 Drawing Sheets

ANTI-HEPARAN SULFATE PEPTIDES THAT BLOCK HERPES SIMPLEX VIRUS INFECTION IN VIVO

CROSS REFERENCE TO RELATED APPLICATIONS

The present application is a divisional of U.S. application Ser. No. 13/842,193, filed Mar. 15, 2013 and titled "Anti-Heparan Sulfate Peptides That Block Herpes Simplex Virus Infection In Vivo," which was a continuation-in-part of International Application No. PCT/US2011/052002, filed Sep. 16, 2011 and titled "Anti-Heparan Sulfate Peptides That Block Herpes Simplex Virus Infection In Vivo," which claims the benefit of U.S. Provisional Patent Application No. 61/383,520, filed Sep. 16, 2010, and the present application also claims the benefit of U.S. Provisional Patent Application No. 61/651,643, filed May 25, 2012, the entire disclosures of which are hereby incorporated by reference in their entireties.

GOVERNMENT SPONSORED RESEARCH OR DEVELOPMENT

This invention was made with government support under R01 Grant Nos. AI057860 awarded by the National Institutes of Health. The government has certain rights in the invention.

SEQUENCE LISTING

The present application includes a Sequence Listing in electronic format as a text file entitled "Sequence_Listing_DA015CIP.txt" which was created on Mar. 14, 2013, and which has a size of 4,601 bytes. The contents of txt file "Sequence_Listing_DA015CIP.txt" are incorporated by reference herein.

BACKGROUND OF THE DISCLOSURE

1. Technical Field

The present disclosure is directed, generally, to the inhibition of viral infection, including herpes simplex virus (HSV) cellular infection, and to the treatment of diseases associated with HSV and other viral infections. More specifically, the present disclosure provides peptides that can block viral infection of a cell both in vitro and in vivo.

2. Description of the Related Art

Heparan sulfate (HS) and its modified form, 3-O sulfated heparan sulfate (3-OS HS) provide cell surface attachment sites for many human and non-human pathogenic viruses, including herpes simplex virus type-1 and -2 (HSV-1 and HSV-2, respectively). HSV infections cause a variety of medical disorders affecting the face and mouth, the eye, the central nervous system, and other areas of the body. Such infections may be especially severe in immunocompromised subjects.

Existing antiviral drugs can reduce the severity of HSV outbreaks, but cannot cure the subject of the infection. Therefore, there is a need for prophylactic agents that can inhibit entry by HSV and other pathogenic viruses into cells. There is also a need for therapeutic agents that can reduce or minimize the spread of HSV and other pathogenic viruses from infected cells to uninfected cells within a subject.

SUMMARY OF THE DISCLOSURE

The present disclosure achieves these and other related needs by providing peptides, including anti-HS peptides and anti-3-OS HS peptides, that significantly inhibit viral infection and/or receptor-mediated cell-to-cell fusion. Exemplified herein are peptides designated G1 and G2, which represent two classes of cationic peptides specifically isolated against HS (e.g., Group 1 peptides) and 3-OS HS (e.g., Group 2 peptides), respectively, and which exhibit strong herpesvirus entry-inhibiting activities. The Group 1 peptides and Group 2 peptides disclosed herein inhibit HSV-1 spread in corneal keratitis thereby demonstrating both the in vivo significance of HS/3-OS HS in HSV-1 pathogenesis as well as the efficacy of the G1 and G2 peptides in the treatment of diseases associated with viral infection.

Also exemplified herein are retro-inverso peptides, designated riG1 and riG2, which represent retro-inverso ("ri") forms of peptides designated G1 and G2, respectively. In some embodiments, a "retro-inverso" form of a peptide has amino acids that are assembled in reverse order ("retro"), and with an inverted ("inverso") chirality (L or D), relative to the peptide. Some retro-inverso peptides may have one or more D-amino acids. In other retro-inverso peptides, all of the amino acids may be D-amino acids. As further described herein, retro-inverso Group 1 peptides and retro-inverso Group 2 peptides may also inhibit viral infection and/or receptor-mediated cell-to-cell fusion, and may be used in the prevention and/or treatment of one or more viral infections. In some embodiments, retro-inverso peptides may have one or more characteristics that enhance their utility for such uses, such as relatively low immunogenicity and/or enhanced resistance to proteolytic degradation, relative to the corresponding G1/G2 peptide.

In various embodiments, peptides described herein may be enriched in basic amino acid residues and classified into two major groups:

(1) Group 1, which includes a class of peptides with alternating charges having the sequence XRXRXKXXRX RX (SEQ ID NO: 2), as represented herein by the G1 peptide having the sequence LRSRTKIIRIRH (SEQ ID NO: 1), and retro-inverso forms of Group 1 peptides, which have a reverse amino acid order XRXRXXKXRXRX (SEQ ID NO: 8) and at least one D-amino acid, as represented herein by the riG1 peptide, which has the sequence HRIRIIKTRSRL (SEQ ID NO: 7) and at least one D-amino acid;

(2) Group 2, which includes a class of peptides with repetitive charges having the sequence

XXRRRRXRRRXK,        (SEQ ID NO: 4)

as represented herein by the G2 peptide having the sequence MPRRRRIRRRQK (SEQ ID NO: 3); and retro-inverso forms of Group 2 peptides, which have a reverse amino acid order

KXRRRXRRRRXX        (SEQ ID NO: 10)

and at least one D-amino acid, as represented herein by the riG2 peptide, which has the sequence KQRRRIRRRRPM (SEQ ID NO: 9) and at least one D-amino acid.

Embodiments of the present disclosure provide peptides that comprise at least 10 or at least 12 consecutive amino acids of the sequence XRXRXKXXRXRX (SEQ ID NO: 2) wherein X is any amino acid, R is arginine, and K is lysine. Within certain aspects, these peptides may be 10 or 12 amino acids in length. Within other aspects, each X may be independently selected from the group consisting of leucine (L), serine (S), threonine (T), isoleucine (I), and histidine (H). Other embodiments of the present disclosure provide peptides that comprise at least 10 or at least 12 consecutive amino acids of the sequence XRXRXXKXRXRX (SEQ ID NO: 8) wherein X is any amino acid, R is arginine, K is lysine, and wherein at least one amino acid is a D-amino acid. Within certain aspects, these peptides may be 10 or 12 amino acids in length. Within other aspects, each X may be independently selected from the group consisting of leucine (L), serine (S), threonine (T), isoleucine (I), and histidine (H). Within still further aspects, these peptides may be composed entirely of D-amino acids.

Some embodiments of the present disclosure provide peptides that comprise at least 10 or at least 12 consecutive amino acids of the peptide G1, which has the amino acid sequence LRSRTKIIRIRH (SEQ ID NO: 1), wherein L is leucine, R is arginine, S is serine, T is threonine, K is lysine, I is isoleucine, and H is histidine. Within certain aspects, these peptides may be 10 or 12 amino acids in length. An exemplary 10 amino acid peptide based upon G1 is the peptide RSRTKIIRIR (SEQ ID NO: 5).

Other embodiments of the present disclosure provide peptides that comprise at least 10 or at least 12 consecutive amino acids of the peptide riG1, which has the amino acid sequence HRIRIIKTRSRL (SEQ ID NO: 7) wherein L is leucine, R is arginine, S is serine, T is threonine, K is lysine, I is isoleucine, H is histidine, and wherein at least one amino acid is a D-amino acid. Within certain aspects, these peptides may be 10 or 12 amino acids in length. An exemplary 10 amino acid peptide based upon riG1 is the peptide RIRIIKTRSR (SEQ ID NO: 11), wherein at least one amino acid is a D-amino acid. In some embodiments, these peptides may be composed entirely of D-amino acids.

Further embodiments of the present disclosure provide peptides that comprise at least 10 or at least 12 consecutive amino acids of the sequence

XXRRRRXRRRXK        (SEQ ID NO: 4)

wherein X is any amino acid, R is arginine, and K is lysine. Within certain aspects, these peptides may be 10 or 12 amino acids in length. Within other aspects, X may be independently selected from the group consisting of methionine (M), proline (P), isoleucine (I), and glutamine (Q). Embodiments of the present disclosure also provide peptides that comprise at least 10 or at least 12 consecutive amino acids of the sequence

KXRRRXRRRXX        (SEQ ID NO: 10)

wherein X is any amino acid, R is arginine, K is lysine and wherein at least one amino acid is a D-amino acid. Within certain aspects, these peptides may be 10 or 12 amino acids in length. Within other aspects, X may be independently selected from the group consisting of methionine (M), proline (P), isoleucine (I), and glutamine (Q). Within still further aspects, these peptides may be composed entirely of D-amino acids.

Other embodiments of the present disclosure provide peptides that comprise at least 10 or at least 12 consecutive amino acids of the peptide G2, which has the amino acid sequence MPRRRRIRRRQK (SEQ ID NO: 3) wherein M is methionine, P is proline, R is arginine, I is isoleucine, Q is glutamine, and K is lysine. Within certain aspects, these peptides may be 10 or 12 amino acids in length. An exemplary 10 amino acid peptide based upon G2 is the peptide RRRRIRRRQK (SEQ ID NO: 6). Still other embodiments of the present disclosure provide peptides that comprise at least 10 or at least 12 consecutive amino acids of the peptide riG2, which has the amino acid sequence KQRRRIRRRRPM (SEQ ID NO: 9) wherein M is methionine, P is proline, R is arginine, I is isoleucine, Q is glutamine, K is lysine and wherein at least one amino acid is a D-amino acid. Within certain aspects, these peptides may be 10 or 12 amino acids in length. An exemplary 10 amino acid peptide based upon riG2 is the peptide KQRRRIRRRR (SEQ ID NO: 12), wherein at least one amino acid is a D-amino acid. Within still further aspects, these peptides may be composed entirely of D-amino acids.

The peptides disclosed herein can block the binding of a virus to heparan sulfate or 3-O sulfated heparan sulfate thereby preventing the viral infection of a target cell, such as a corneal cell. Viruses the binding of which can be blocked by these peptides include herpesviruses, such as a herpesvirus selected from the group consisting of an α-herpesvirus, a β-herpesvirus, and a γ-herpesvirus. Within certain aspects, the α-herpesvirus is HSV-1. Within other aspects, the β-herpesvirus is cytomegalovirus (CMV). Within still further aspects, the γ-herpesvirus is human herpesvirus-8 (HHV-8).

In some embodiments, the peptides disclosed herein may be combined into compositions comprising two or more peptides, wherein each of the peptides independently comprises at least 10 amino acids of a sequence selected from the group consisting of

| XRXRXKXXRXRX, | (SEQ ID NO: 2) |
| XRXRXXKXRXRX, | (SEQ ID NO: 8) |
| XXRRRRXRRRXK, and | (SEQ ID NO: 4) |
| KXRRRXRRRXX, | (SEQ ID NO: 10) | wherein X is any amino acid, R is arginine, and K is lysine. In some embodiments, each X is independently selected from the group consisting of leucine, serine, threonine, isoleucine, methionine, proline, glutamine, and histidine. In other embodiments, at least one of said peptides comprises at least 10 consecutive amino acids of a sequence selected from the group consisting of LRSRTKIIRIRH (SEQ ID NO: 1), HRIRIIKTRSRL (SEQ ID NO: 7), MPRRRRIRRRQK (SEQ ID NO: 3), and KQRRRIRRRRPM (SEQ ID NO: 9). In some embodiments, one or more of the peptides may comprise at least 12 consecutive amino acids of the selected sequence. In other embodiments, one or more of the peptides is 10-12 amino acids in length. In some aspects of these compositions, one or more of the amino acids is a D-amino acid. In other aspects of these compositions, all of the amino acids of at least one of the peptides may be D-amino acids.

In other embodiments, peptides disclosed herein may be combined into compositions comprising two or more peptides wherein each of the peptides independently comprises at least 10 amino acids of a sequence selected from the group consisting of

| XRXRXKXXRXRX and | (SEQ ID NO: 2) |
| XXRRRRXRRRXK | (SEQ ID NO: 4) | wherein X is any amino acid, R is arginine, and K is lysine. In some embodiments, each X is independently selected from the group consisting of leucine, serine, threonine, isoleucine, methionine, proline, glutamine, and histidine.

Within certain aspects of these compositions, at least one of the peptides comprises at least 10 amino acids of the sequence LRSRTKIIRIRH (SEQ ID NO: 1), such as the peptide RSRTKIIRIR (SEQ ID NO: 5). Within other aspects of these compositions, at least one of the peptides comprises at least 10 amino acids of the sequence MPRRRRIRRRQK (SEQ ID NO: 3), such as the peptide RRRRIRRRQK (SEQ ID NO: 6). In still further aspects of these compositions, one or more of the peptides includes at least one D-amino acid.

In other embodiments, peptides disclosed herein may be combined into compositions comprising two or more peptides wherein each of the peptides independently comprises at least 10 amino acids of a sequence selected from the group consisting of

```
XRXRXXKXRXRX        (SEQ ID NO: 8)
and

KXRRRXRRRRXX,       (SEQ ID NO: 10)
``` wherein X is any amino acid, R is arginine, K is lysine, and at least one amino acid is a D-amino acid. In some embodiments, each X is independently selected from the group consisting of leucine, serine, threonine, isoleucine, methionine, proline, glutamine, and histidine. Within certain aspects of these compositions, each of the peptides independently comprises at least 10 amino acids of a sequence selected from the group consisting of HRIRIIKTRSRL (SEQ ID NO: 7), such as the peptide RIRIIKTRSR (SEQ ID NO: 11), wherein at least one amino acid is a D-amino acid. Within other aspects of these compositions, at least one of the peptides comprises at least 10 amino acids of the sequence KQRRRIRRRRPM (SEQ ID NO: 9), such as the peptide KQRRRIRRRR (SEQ ID NO: 12), wherein at least one amino acid is a D-amino acid. Within still further aspects, one or more of these peptides is composed entirely of D-amino acids.

In other embodiments, peptides disclosed herein may be combined into compositions comprising two or more peptides wherein one of the peptides comprises at least 10 amino acids of a sequence selected from the group consisting of

```
XRXRXKXXRXRX        (SEQ ID NO: 2)
and

XXRRRRXRRRXK,       (SEQ ID NO: 4)
``` and another one of the peptides comprises at least 10 amino acids of the sequence selected from the group consisting of

```
XRXRXXKXRXRX        (SEQ ID NO: 8)
and

KXRRRXRRRRXX,       (SEQ ID NO: 10)
``` wherein X is any amino acid, R is arginine, and K is lysine. In some embodiments, each X is independently selected from the group consisting of leucine, serine, threonine, isoleucine, methionine, proline, glutamine, and histidine. In certain aspects of such compositions, at least one of the peptides comprises at least 10 amino acids of the sequence LRSRTKIIRIRH (SEQ ID NO: 1), such as the peptide RSRTKIIRIR (SEQ ID NO: 5), or at least 10 amino acids of the sequence MPRRRRIRRRQK (SEQ ID NO: 3), such as the peptide RRRRIRRRQK (SEQ ID NO: 6), and another one of the peptides comprises at least 10 amino acids of a sequence selected from the group consisting of HRIRIIKTRSRL (SEQ ID NO: 7), such as the peptide RIRIIKTRSR (SEQ ID NO: 11), or at least 10 amino acids of the sequence KQRRRIRRRRPM (SEQ ID NO: 9), such as the peptide KQRRRIRRRR (SEQ ID NO: 12), wherein at least one amino acid is a D-amino acid. Within still further aspects, one or more of these peptides is composed entirely of D-amino acids.

Other embodiments provide methods for blocking the binding of a virus to a target cell. Embodiments of such methods may include contacting the target cell with a peptide such as a G1, riG1, G2, or riG2 peptide. In some embodiments, a method for blocking the binding of a virus to a target cell may comprise contacting the target cell with a peptide comprising at least 10 or at least 12 consecutive amino acids of a sequence selected from the group consisting of

```
XRXRXKXXRXRX,       (SEQ ID NO: 2)

XRXRXXKXRXRX,       (SEQ ID NO: 8)

XXRRRRXRRRXK,       (SEQ ID NO: 4)
and

KXRRRXRRRRXX,       (SEQ ID NO: 10)
``` wherein X is any amino acid, R is arginine, and K is lysine. In some embodiments, each X is independently selected from the group consisting of leucine, serine, threonine, isoleucine, methionine, proline, glutamine, and histidine. Optionally, at least one amino acid may be a D-amino acid. In other embodiments, a method for blocking the binding of a virus to a target cell may include contacting the target cell with a peptide comprising at least 10 or at least 12 consecutive amino acids of a sequence selected from the group consisting of LRSRTKIIRIRH (SEQ ID NO: 1), HRIRIIKTRSRL (SEQ ID NO: 7), MPRRRRIRRRQK (SEQ ID NO: 3), and KQRRRIRRRRPM (SEQ ID NO: 9). In other embodiments, a method for blocking the binding of a virus to a target cell may include contacting the target cell with a peptide comprising a sequence selected from the group consisting of RSRTKIIRIR (SEQ ID NO: 5), RRRRIRRRQK (SEQ ID NO: 6), RIRIIKTRSR (SEQ ID NO: 11), and KQRRRIRRRR (SEQ ID NO: 12). In some embodiments, the peptide comprises at least 10 consecutive amino acids of the selected sequence. In other embodiments, the peptide comprises at least 12 consecutive amino acids of the selected sequence. In other embodiments, the peptide is 10-12 amino acids in length.

In other embodiments, a method for blocking the binding of a virus to a target cell may include contacting the target cell with a peptide comprising at least 10 or at least 12 consecutive amino acids of the sequence XRXRXKXXRXRX (SEQ ID NO: 2) wherein X is any amino acid, R is arginine, and K is lysine. In some embodiments, each X is independently selected from the group consisting of leucine, serine, threonine, isoleucine, methionine, proline, glutamine, and histidine. Within certain aspects of these methods, the peptide comprises at least 10 or at least 12 consecutive amino acids of the sequence LRSRTKIIRIRH (SEQ ID NO: 1). For example, in some embodiments the peptide may comprise the sequence RSRTKIIRIR (SEQ ID NO: 5). Optionally the peptide may comprise one or more D-amino acids.

In some embodiments, a method for blocking the binding of a virus to a target cell may include contacting the target cell with a peptide comprising at least 10 or at least 12 consecutive amino acids of the sequence XRXRXXKXRX RX (SEQ ID NO: 8) wherein X is any amino acid, R is arginine, K is lysine, and wherein at least one amino acid is a D-amino acid. In some embodiments, each X is independently selected from the group consisting of leucine, serine, threonine, isoleucine, methionine, proline, glutamine, and histidine. Within certain aspects of these methods, the peptide comprises at least 10 or at least 12 consecutive amino acids of the sequence HRIRIIKTRSRL (SEQ ID NO: 7), wherein at least one amino acid is a D-amino acid. For example, in some embodiments the peptide may comprise the sequence RIRIIKTRSR (SEQ ID NO: 11), wherein at least one amino acid is a D-amino acid. Within still further aspects, these peptides may be composed entirely of D-amino acids.

In further embodiments, a method for blocking the binding of a virus to a target cell may include contacting the target cell with a peptide comprising at least 10 or at least 12 consecutive amino acids of the sequence

XXRRRRXRRRXK    (SEQ ID NO: 4)

wherein X is any amino acid, R is arginine, and K is lysine. In some embodiments, each X is independently selected from the group consisting of leucine, serine, threonine, isoleucine, methionine, proline, glutamine, and histidine. Within certain aspects of these methods, the peptide comprises at least 10 or at least 12 consecutive amino acids of the sequence MPRRRRIRRRQK (SEQ ID NO: 3), the peptide may comprise the sequence RRRRIRRRQK (SEQ ID NO: 6). Optionally, the peptide may include one or more D-amino acids.

Other embodiments of a method for blocking the binding of a virus to a target cell may include contacting the target cell with a peptide comprising at least 10 or at least 12 consecutive amino acids of the sequence

KXRRRXRRRRXX,    (SEQ ID NO: 10)

wherein X is any amino acid, R is arginine, and K is lysine and wherein at least one amino acid is a D-amino acid. In some embodiments, each X is independently selected from the group consisting of leucine, serine, threonine, isoleucine, methionine, proline, glutamine, and histidine. Within certain aspects of these methods, the peptide comprises at least 10 or at least 12 consecutive amino acids of the sequence KQRRRIRRRRPM (SEQ ID NO: 9), wherein at least one amino acid is a D-amino acid. For example, in some embodiments the peptide may comprise the sequence KQRRRIRRRR (SEQ ID NO: 12), wherein at least one amino acid is a D-amino acid. Within still further aspects, these peptides may be composed entirely of D-amino acids.

Methods, peptides, compositions, and conjugates described herein may be effective to block or inhibit target cell binding by one more viruses. Such viruses may include pathogenic viruses with target cell entry mechanisms/strategies that include binding to HS on target cell surfaces. Viruses for which target cell entry can be blocked or inhibited by peptides and methods described herein may include one or more herpesviruses. In some embodiments, such peptides and methods may be effective to block or inhibit target cell entry by one or more herpesviruses, wherein each herpesvirus is selected from the group consisting of an α-herpesvirus, a β-herpesvirus, and a γ-herpesvirus. Within certain aspects, the α-herpesvirus is HSV-1.

Within other aspects, the β-herpesvirus is cytomegalovirus (CMV). Within yet other aspects, the γ-herpesvirus is human herpesvirus-8 (HHV-8).

Embodiments of the present disclosure provide methods for the treatment of a patient who is susceptible to a viral infection. In some embodiments, methods for the treatment of a patient who is susceptible to a viral infection may include administering to the patient a peptide comprising at least 10 consecutive amino acids of a sequence selected from the group consisting of a sequence selected from the group consisting of

| XRXRXKXXRXRX,   | (SEQ ID NO: 2)  |
|-----------------|-----------------|
| XRXRXXKXRXRX,   | (SEQ ID NO: 8)  |
| XXRRRRXRRRXK,   | (SEQ ID NO: 4)  |
| and             |                 |
| KXRRRXRRRRXX,   | (SEQ ID NO: 10) | wherein X is any amino acid, R is arginine, and K is lysine. In some embodiments, each X is independently selected from the group consisting of leucine, serine, threonine, isoleucine, methionine, proline, glutamine, and histidine. Optionally, at least one amino acid may be a D-amino acid.

In other embodiments, methods for the treatment of a patient who is susceptible to a viral infection may include administering to the patient a peptide comprising at least 10 or at least 12 consecutive amino acids of a sequence selected from the group consisting of LRSRTKIIRIRH (SEQ ID NO: 1), HRIRIIKTRSRL (SEQ ID NO: 7), MPRRRRIRRRQK (SEQ ID NO: 3), and KQRRRIRRRRPM (SEQ ID NO: 9). In other embodiments, methods for the treatment of a patient who is susceptible to a viral infection may include administering to the patient a peptide comprising a sequence selected from the group consisting of RSRTKIIRIR (SEQ ID NO: 5), RRRRIRRRQK (SEQ ID NO: 6), RIRIIKTRSR (SEQ ID NO: 11), and KQRRRIRRRR (SEQ ID NO: 12). In some embodiments, the peptide comprises at least 10 consecutive amino acids of the selected sequence. In other embodiments, the peptide comprises at least 12 consecutive amino acids of the selected sequence. In other embodiments, the peptide is 10-12 amino acids in length.

In other embodiments, methods for the treatment of a patient who is susceptible to a viral infection may include administering to the patient a peptide comprising at least 10 or at least 12 consecutive amino acids of the sequence XRX RXKXXRXRX (SEQ ID NO: 2) wherein X is any amino acid, R is arginine, and K is lysine. In some embodiments, each X is independently selected from the group consisting of leucine, serine, threonine, isoleucine, methionine, proline, glutamine, and histidine. Within certain aspects of these methods, the peptide comprises at least 10 or at least 12 consecutive amino acids of the sequence LRSRTKIIRIRH (SEQ ID NO: 1). For example, in some embodiments the peptide may comprise the sequence RSRTKIIRIR (SEQ ID NO: 5). Optionally, the peptide may comprise one or more D-amino acids.

Still further embodiments of the present disclosure provide methods for the treatment of a patient who is susceptible to a viral infection wherein the methods comprise the step of administering to the patient a peptide comprising at least 10 consecutive amino acids of the sequence XRXRXX KXRXRX (SEQ ID NO: 8) wherein X is any amino acid, R is arginine, K is lysine, and wherein at least one amino acid is a D-amino acid. In some embodiments, each X is independently selected from the group consisting of leucine, serine, threonine, isoleucine, methionine, proline, glutamine, and histidine. In certain aspects of these methods, the peptide comprises at least 10 or at least 12 consecutive amino acids of the sequence HRIRIIKTRSRL (SEQ ID NO: 7), wherein at least one amino acid is a D-amino acid. For example, in some embodiments the peptide may include the sequence RIRIIKTRSR (SEQ ID NO: 11), wherein at least one amino acid is a D-amino acid. Within still further aspects, these peptides may be composed entirely of D-amino acids. Related embodiments of the present disclosure provide methods for the treatment of a patient who is susceptible to a viral infection wherein the methods comprise administering to the patient a peptide comprising at least 10 consecutive amino acids of the sequence

XXRRRXRRRXK (SEQ ID NO: 4)

wherein X is any amino acid, R arginine, and K is lysine. In some embodiments, each X is independently selected from the group consisting of leucine, serine, threonine, isoleucine, methionine, proline, glutamine, and histidine. Within certain aspects of these methods, the peptide comprises at least 10 or at least 12 consecutive amino acids of the sequence MPRRRRIRRRQK (SEQ ID NO: 3). For example, in some embodiments, the peptide may comprise the sequence RRRRIRRRQK (SEQ ID NO: 6). Optionally, the peptide may include one or more D-amino acids.

Other embodiments of methods for the treatment of a patient who is susceptible to a viral infection may include administering to the patient a peptide comprising at least 10 or at least 12 consecutive amino acids of the sequence

KXRRRXRRRXX, (SEQ ID NO: 10)

wherein X is any amino acid, R is arginine, and K is lysine and wherein at least one amino acid is a D-amino acid. In some embodiments, each X is independently selected from the group consisting of leucine, serine, threonine, isoleucine, methionine, proline, glutamine, and histidine. Within certain aspects of these methods, the peptide comprises at least 10 or at least 12 consecutive amino acids of the sequence KQRRRIRRRRPM (SEQ ID NO: 9), wherein at least one amino acid is a D-amino acid. For example, in some embodiments the peptide may comprise the sequence KQRRRIRRRR (SEQ ID NO: 12), wherein at least one amino acid is a D-amino acid. Within still further aspects, these peptides may be composed entirely of D-amino acids.

Yet further embodiments of the present disclosure provide HS and 3-OS HS binding peptide-therapeutic compound conjugates that comprise an HS or a 3-OS binding peptide, as summarized above and as described in greater detail below, that is coupled to a therapeutic compound, such as an antiviral compound selected from a nucleoside analog, an oligosaccharide, and a small molecule.

Within certain aspects of these embodiments, nucleoside analogs that may be used in these HS and 3-OS HS binding peptide-therapeutic compound conjugates include guanosine analogs such as acyclovir (Formula I) and valacyclovir.

Formula I

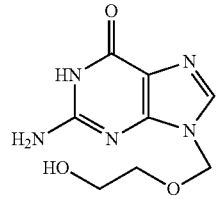

Within other aspects of these embodiments, oligosaccharides that may be used in these HS and 3-OS HS binding peptide-therapeutic compound conjugates include oligosaccharides such as tetrasaccharides, hexasaccharides, octasaccharides, and decasaccharides that are capable of binding to one or more of HSV-1 glycoproteins gB, gC, and gD. For example an oligosaccharide can be an HS octasaccharide 1 having the structure of Formula II:

Formula II

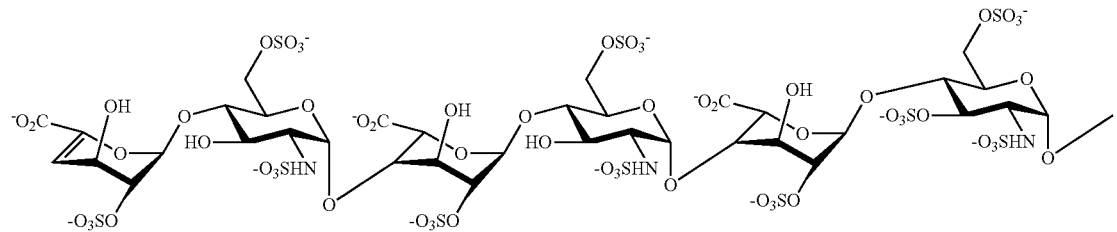

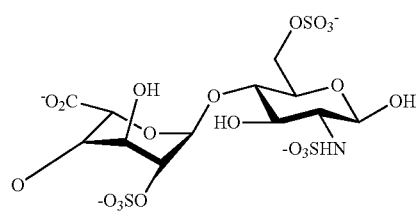

Within still further aspects of these embodiments, small molecules that may be used in these HS and 3-OS HS binding peptide-therapeutic compound conjugates include Bis-2-methyl-4-amino-quinolyl-6-carbamide (Surfen) having the structure of Formula III:

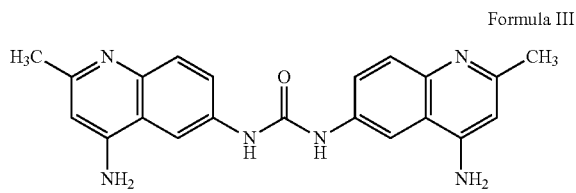

Formula III

DETAILED DESCRIPTION OF THE DISCLOSURE

Figure 1:
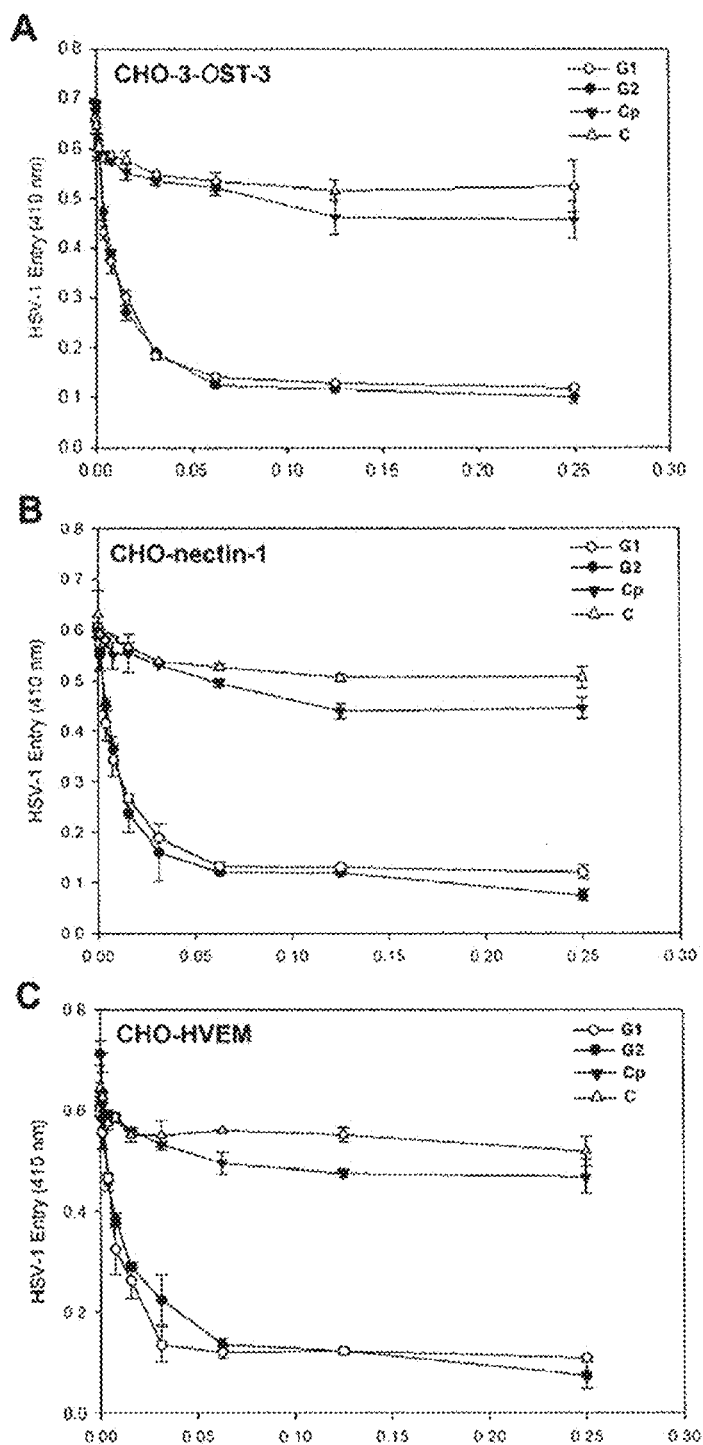
FIG. 1 demonstrates that the inhibition of HSV-1 entry by 12-mer synthetic peptides is not specific to any particular gD receptor.

The present disclosure is based upon the unexpected discovery that certain peptides, including certain 10-mer and 12-mer peptides, can specifically bind to HS and 3-OS HS and can block the entry of a virus, such as a herpes simplex virus (e.g., HSV-1), into a target cell.

Heparan sulfate (HS) and its modified form, 3-O sulfated heparan sulfate (3-OS HS), when present on a cell surface, may provide an attachment site for human and non-human pathogenic viruses such as herpes simplex virus type-1 and -2 (HSV-1 and HSV-2, respectively) thereby contributing to viral infections. Both wild-type and laboratory strains of HSV bind to HS. In addition to the attachment step, HSV-1 penetration into cells can also be mediated by 3-OS HS, which is produced after a rare enzymatic modification in HS catalyzed by 3-O-sulfortransferases (3-OSTs).

HSV envelope glycoproteins B and C (gB and gC) bind HS and mediate virus attachment to cells. A third glycoprotein, gD, specifically recognizes 3-OS HS in a binding interaction that facilitates fusion pore formation during viral entry. Despite the known importance of HS and 3-OS HS during HSV-1 infection in vitro, little is known about the significance of HS and 3-OS during an infection in vivo.

The versatility of HS to bind multiple microbes and participate in a variety of regulatory phenomena comes from its negatively-charged nature and highly complex structure, which is generated by enzymatic modifications. Virtually all cells express HS as long un-branched chains often associated with protein cores commonly exemplified by syndecan and glypican families of HS proteoglycans. The parent HS chain, which contains repeating glucosamine and hexuronic acid dimers, can be 100-150 residues long and may contain multiple structural modifications. Most common among these structural modifications is the addition of sulfate groups at various positions within the chain, which leads to the generation of specific motifs, making HS highly attractive for microbial adherence.

The role of HS in viral infection may extend beyond its function as a low-specificity pre-attachment site. For instance, HS mediates HSV-1 transport on filopodia during surfing and negatively regulates virus-induced membrane fusion. Likewise, for human papilloma virus (HPV), HS proteoglycans play a key role in the activation of immune response, an important aspect for both vaccine development and HPV pathogenesis. Similarly, HS expressed on spermatozoa plays a key role in the capture of human immunodeficiency virus (HIV) and its transmission to dendritic, macrophage, and T-cells. 3OS HS also plays a role in hepatitis B virus replication, and HS-binding peptides or compounds can be used to prevent genital HPV, HIV, and cytomegalovirus infections.

The results of viral entry and gD-binding assays and the fluorescent microscopy data presented herein demonstrate that both G1 and G2 are potent in blocking viral entry, in particular HSV-1 entry, into primary cultures of human corneal fibroblasts (CF) and CHO-K1 cells transiently expressing different gD-receptors. Moreover, the G2 peptide, which was isolated against 3-OS HS, displays a wider ability to inhibit the entry of clinically relevant strains of HSV-1, and some divergent members of herpesvirus family including cytomegalovirus (CMV) and human herpesvirus-8 (HHV-8).

The entry blocking activity of the peptides disclosed herein is independent of gD receptor, virus strain, or cell-type. In addition to G1 and G2 peptides, the present disclosure provides retro-inverso forms of the G1 and G2 peptides, riG1 and riG2 respectively, in which all L-amino acids are replaced with D-amino acids and the change in chirality counterbalanced by reversing the primary sequence. Without being bound by theory, it is believed that the G1 and G2 peptides function by interfering with viral binding to a cell, and that retro-inverso forms thereof (e.g., riG1 and riG2) will also interfere with viral binding to cells.

Utility of Anti-HS and Anti-3-OS HS Peptides

As described in greater detail herein, the anti-HS and anti-3-OS peptides of the present disclosure will find broad utility in preventing viral infection of a target cell, both in vivo and in vitro. Thus, for example, anti-HS and anti-3-OS peptides will find therapeutic utility as efficacious compounds for the treatment of a viral disease, such as a herpesvirus-mediated disease including an α-herpesvirus-, a β-herpesvirus-, and/or a γ-herpesvirus-mediated disease.

The anti-HS and anti-3-OS peptides disclosed herein will also find utility in studies seeking to demonstrate the significance of HS during in vivo viral infection, such as HSV-1 infection. HS has been studied as an attachment receptor, but little has been reported on its function in vivo. The experiments presented herein, including experiments with a mouse corneal infection model, demonstrate the efficacy of the G1 and G2 peptides in blocking infection in vivo and indicate that HS is an important HSV-1 co-receptor both in vitro and in vivo.

The ability of the presently disclosed peptides to act specifically on HS/3-OS HS is significant because HS is widely expressed on all cells and tissues and it is known to regulate many important biological phenomena. Thus, the presently disclosed peptides can be used to prevent the infection of a wide range of cells and tissues, both in vitro and in vivo, and as probes to study HS functions in a wide variety of biological contexts.

Additionally, HS moieties are frequently up-regulated during pathological conditions and may contribute to inflammation. Thus, the presently disclosed peptides may also find utility in blocking the pathological effects of HS and in regulating inflammation.

The complex enzymatic regulation of HS chain gives HS a complex ability (and affinity) to bind many proteins to perform new functions. Therefore, 3-OS HS binding peptides disclosed herein will be useful as probes and/or as diagnostic tools to assess structural alterations within HS or its turnover on cell surfaces.

Because many unrelated viruses bind HS, the G1 and G2 peptides as well as their retro-inverso forms (riG1 and riG2 peptides) will find broad utility in those applications where it is desired to block infection by a wide variety of viruses that utilize HS and/or 3-OS HS binding to facilitate target cell binding and infection.

These and other utilities are contemplated by the presently disclosed anti-HS and anti-3-OS peptides, including the Group 1 and Group 2 peptides G1 and G2, as well as the retro-inverso forms of these peptides riG1 and riG2, which are described in substantial detail herein.

Anti-Heparan Sulfate and Anti-3-O Sulfated Heparan Sulfate Peptides

As summarized above, the present disclosure provides peptides that were identified by the screening of a random M13-phage display library with heparan sulfate and 3-O sulfated heparan sulfate and the subsequent isolation of HS- and 3-O sulfated HS binding phages. The peptides disclosed herein, which are exemplified by those peptides that are presented in Table 1, are characterized by the presence of the positively charged amino-acid residues arginine and/or lysine, the unique arrangement of which is important for blocking virus-cell binding and/or virus-induced membrane fusion.

TABLE 1

Amino acid (AA) Sequences of Phage-displayed Peptides Isolated by Three Round Screening against HS and 3-OS HS AA sequences of peptides against HS

| | | | |
|---|---|---|---|
| PVFRNIRVGDPI$^1$ | RLPRLKMRNRG$^3$ | HKRRRQLRIQRR$^5$ | QRNHILTPGTSI$^2$ |
| CGGLDSGSGVLA$^1$ | NHRPLLIRRRRT$^5$ | RLNNPRLLNTRP$^3$ | LMSLRKTNRINM$^2$ |
| LFGILLCGVIYV$^1$ | RKPRTSPSITLR$^3$ | KLHMRHHRSPRI$^5$ | RSMHHINRRQRR$^4$ |
| DLGSLYVGGACG$^1$ | PRRNLRRRRLIP$^4$ | IRKRRLRHQPRS$^4$ | RSPSQQSIMPLH$^3$ |
| RVCGSIGKEVLG$^2$ | LRSRTKIIRIRH$^{8}$** | RPRTRLHTHRNR$^4$ | PRKRRRTQQRRI$^6$ |
| CGILGESGGVLI$^1$ | HILIRIRRQRTP$^4$ | MNPTRRSRMRMI$^3$ | SKRSNQPIINR$^2$ |
| VFRINNIRVGDY$^1$ | RLRRLIRNRGT$^3$ | RRRTQRKRRHTI$^6$ | IIQLSRRLRSIR$^3$ |

AA sequences of peptides against 3-OS HS

| | | | |
|---|---|---|---|
| RINKLDVLIIPV$^1$ | MPRRRRIRRRQK$^{11}$** | QPRHKQIPIKML$^3$ | NNNSPMRRSRNH$^2$ |
| LICGRVINKINK$^1$ | QKNIRRRSRSKL$^6$ | QRKTRIPRSTLP$^4$ | KRNRRPIKLRHS$^5$ |
| CCGIIEVTQLGK$^1$ | RKIISLTNRRLS$^4$ | RRLSSMWNLMKN$^3$ | KPQTLSIRPQLI$^3$ |
| RGLSQKKRHIIQ$^1$ | QLRKRQIIRSQQ$^2$ | HIIPKRTLRRNI$^4$ | RTIPNRIKTIPM$^4$ |
| HRIKLVAAIDVG$^1$ | LMSLRKTNRINIM$^2$ | RSNPKKSRSLQM$^4$ | INLTSKRMSLRN$^3$ |
| GGCTKHIDVALK$^1$ | KRSIIQINPTQS$^2$ | TPHRRHIITPSN$^3$ | IRRHRRRLSQII$^6$ |
| RFQKIDLIATRQ$^1$ | RKINIQRRSTLM$^4$ | PTQLHKRPRIRL$^4$ | HRPRLKMRRPTM$^5$ |

G1 peptide isolated against HS
G2 peptide isolated against 3OS HS
$^n$Frequency/number of times peptide sequences isolated;
**P < 0.001, Frequently isolated peptides.

The peptides that are described herein are enriched in basic amino acid residues and classified into two major groups:

(1) Group 1, which includes a class of peptides having alternating charges (XRXRXKXXRXRX; SEQ ID NO: 2) and is represented herein by the G1 peptide, which has the amino acid sequence LRSRTKIIRIRH (SEQ ID NO: 1); and the retro-inverso forms of the Group 1 peptides, which includes the peptides having the sequence XRXRXXKXRXRX (SEQ ID NO: 8), wherein at least one amino acid is a D-amino acid, and is represented herein by the riG1 peptide, which has the amino acid sequence HRIRIIKTRSRL (SEQ ID NO: 7), wherein at least one amino acid is a D-amino acid;

(2) Group 2, which includes a class of peptides having repetitive charges (XXRRRRXRRRXK; SEQ ID NO: 4)

and is represented herein by the G2 peptide, which has the amino acid sequence MPRRRRIRRRQK (SEQ ID NO: 3); and the retro-inverso forms of the Group 2 peptides, which includes the peptides having the sequence (SEQ ID NO: 10)
KXRRRXRRRRXX, wherein at least one amino acid is a D-amino acid, and is represented herein by the riG2 peptide, which has the amino acid sequence KQRRRIRRRRPM (SEQ ID NO: 9), wherein at least one amino acid is a D-amino acid.

Group 1 peptides of the present disclosure comprise at least 10 or at least 12 consecutive amino acids of the sequence XRXRXKXXRXRX (SEQ ID NO: 2) wherein X is any amino acid, R is arginine, and K is lysine. Within certain Group 1 peptides, X may be independently selected from the group consisting of leucine, serine, threonine, isoleucine, and histidine. The retro-inverso Group 1 peptides of the present disclosure comprise at least 10 or at least 12 consecutive amino acids of the sequence XRXRXXKXRX RX (SEQ ID NO: 8) wherein X is any amino acid, R is arginine, K is lysine, and wherein at least one amino acid is a D-amino acid. Within certain retro-inverso Group 1 peptides, X may be independently selected from the group consisting of leucine, serine, threonine, isoleucine, and histidine. In some aspects, these retro-inverso peptides may be composed entirely of D-amino acids.

Exemplified herein are Group 1 peptides that are 10, 11, or 12 amino acids in length, such as peptides that comprise at least 10 or at least 12 consecutive amino acids of the sequence LRSRTKIIRIRH (G1; SEQ ID NO: 1) wherein L is leucine, R is arginine, S is serine, T is threonine, K is lysine, I is isoleucine, and H is histidine. Also exemplified herein are retro-inverso Group 1 peptides that are 10, 11, or 12 amino acids in length, such as peptides that comprise at least 10 or at least 12 consecutive amino acids of the sequence HRIRIIKTRSRL (riG1; SEQ ID NO: 7) wherein L is leucine, R is arginine, S is serine, T is threonine, K is lysine, I is isoleucine, and H is histidine and wherein at least one amino acid is a D-amino acid. In some aspects, a retro-inverso peptide may be composed entirely of D-amino acids.

Group 2 peptides of the present disclosure comprise at least 10 or at least 12 consecutive amino acids of the sequence (SEQ ID NO: 4)
XXRRRRXRRRXK wherein X is any amino acid, R is arginine, and K is lysine. Within certain Group 2 peptides, X may be independently selected from the group consisting of methionine, proline, isoleucine, and glutamine. The retro-inverso Group 2 peptides of the present disclosure comprise at least 10 or at least 12 consecutive amino acids of the sequence (SEQ ID NO: 10)
KXRRRXRRRRXX wherein X is any amino acid, R is arginine, and K is lysine and wherein at least one amino acid is a D-amino acid. Within certain retro-inverso Group 2 peptides, X may be independently selected from the group consisting of methionine, proline, isoleucine, and glutamine. In some aspects, these retro-inverso peptides may be composed entirely of D-amino acids.

Exemplified herein are Group 2 peptides that are 10, 11, or 12 amino acids in length, such as peptides that comprise at least 10 or at least 12 consecutive amino acids of the sequence MPRRRRIRRRQK (SEQ ID NO: 3) wherein M is methionine, P is proline, R is arginine, I is isoleucine, Q is glutamine, and K is lysine. Also exemplified herein are retro-inverso Group 2 peptides that are 10, 11, or 12 amino acids in length, such as peptides that comprise at least 10 or at least 12 consecutive amino acids of the sequence KQR-RRIRRRRPM (riG2; SEQ ID NO: 9) wherein M is methionine, P is proline, R is arginine, I is isoleucine, Q is glutamine, and K is lysine and wherein at least one amino acid is a D-amino acid. In some aspects, these retro-inverso peptides may be composed entirely of D-amino acids.

The peptides disclosed herein can block binding of a virus to heparan sulfate or 3-O sulfated heparan sulfate and/or can prevent a viral infection of a target cell, such as a corneal cell. Viruses the binding of which can be blocked by these peptides include herpesviruses, such as α-herpesviruses, β-herpesviruses, and γ-herpesviruses. Within certain aspects, the α-herpesvirus is HSV-1. Within other aspects, the β-herpesvirus is cytomegalovirus (CMV). Within still further aspects, the γ-herpesvirus is human herpesvirus-8 (HHV-8).

While the G1 and G2 peptides represent specific examples of Group 1 and Group 2 peptides, respectively, it will be understood that alternative Group 1 and Group 2 peptides may be identified by the identification of alternative functional amino acids. For example, alternative functional amino acids within Group 1 and Group 2 peptides can be identified through the generation of point mutations and/or via alanine scanning mutagenesis. Similarly, while the riG1 and riG2 peptides represent specific examples of retro-inverso Group 1 and retro-inverso Group 2 peptides, respectively, it will be understood that alternative retro-inverso Group 1 and retro-inverso Group 2 peptides may be identified by the identification of alternative functional amino acids. For example, alternative functional amino acids within retro-inverso Group 1 and retro-inverso Group 2 peptides can also be identified through the generation of point mutations and/or via alanine scanning mutagenesis.

It is disclosed herein that, while both G1 and G2 peptides are capable of blocking HSV-1-mediated cell binding and infection, G2 exhibits the additional capacity to block the entry of divergent herpesviruses such as, for example, CMV and HHV-8. Without being limited by theory, because the G2 peptide can block membrane fusion it is believed that the G2 peptide can interfere with gD's interaction with its receptor, 3-OS HS. Among the structural differences between G1 and G2, it appears that G2 shows more dependence on the positively charged residues than G1, which may depend upon the presence of a lysine residue at the N-terminus. In general, arginine has been found important for charge-charge interaction with HS.

The peptides disclosed herein can be combined into compositions comprising one, two, or more peptides wherein each of the peptides independently comprises at least 10 amino acids of the amino acid sequences XRXRXKXXXRXRX (SEQ ID NO: 2)
and/or

XXRRRRXRRRXK. (SEQ ID NO: 4)

Exemplified herein are compositions comprising one or more peptides each of which includes at least 10 amino acids of the sequence LRSRTKIIRIRH (SEQ ID NO: 1) and/or at least 10 amino acids of the sequence MPRRRRIRRRQK (SEQ ID NO: 3).

The peptides disclosed herein can be combined into compositions comprising one, two, or more peptides wherein each of the peptides independently comprises at least 10 amino acids of the amino acid sequences XRXRXX KXRXRX (SEQ ID NO: 8), wherein at least one amino acid is a D-amino acid, and/or

KXRRRXRRRXX, (SEQ ID NO: 10)

wherein at least one amino acid is a D-amino acid. Exemplified herein are compositions comprising one or more peptides each of which includes at least 10 amino acids of the sequence HRIRIIKTRSRL (SEQ ID NO: 7), wherein at least one amino acid is a D-amino acid, and/or at least 10 amino acids of the sequence KQRRRIRRRRPM (SEQ ID NO: 9), wherein at least one amino acid is a D-amino acid. Further exemplified herein are compositions comprising one or more peptides each of which includes at least 10 amino acids of the sequence HRIRIIKTRSRL (SEQ ID NO: 7), wherein all the amino acids are D-amino acids, and/or at least 10 amino acids of the sequence KQRRRIRRRRPM (SEQ ID NO: 9), wherein all the amino acids are D-amino acids.

The peptides of the present disclosure can be provided to a patient as part of a pharmaceutical composition where it is mixed with a pharmaceutically acceptable carrier. As used herein, the term "pharmaceutical composition" refers to a preparation of one or more of the peptides described herein with one or more other chemical component(s) such as a physiologically suitable carrier or excipient. The purpose of a pharmaceutical composition is to facilitate administration of a compound to the patient. Techniques for formulation and administration of compositions can be found in "Remington's Pharmaceutical Sciences," Mack Publishing Co., Easton, Pa.

As used herein, the phrases "physiologically acceptable carrier" and "pharmaceutically acceptable carrier" refer to a carriers, diluents, and/or adjuvants that do not cause significant irritation to a patient and do not abrogate the biological activity and properties of the administered peptide. Suitable carriers may include polyethylene glycol (PEG), a biocompatible polymer with a wide range of solubility in both organic and aqueous media.

As used herein, the term "excipient" refers to an inert substance added to a pharmaceutical composition to further facilitate administration of an active peptide. Exemplary excipients include calcium carbonate, calcium phosphate, various sugars and types of starch, cellulose derivatives, gelatin, vegetable oils and polyethylene glycols.

Pharmaceutical compositions can be manufactured by processes well known in the art such as, for example, by means of conventional mixing, dissolving, granulating, dragee-making, levigating, emulsifying, encapsulating, entrapping or lyophilizing processes. Pharmaceutical compositions can be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active peptides of the disclosure may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

Compositions of the present disclosure that are suitable for oral administration may be prepared as capsules, cachets, tablets or lozenges, each containing a predetermined amount of the peptide of the invention, or which may be contained in liposomes or as a suspension in an aqueous liquor or non-aqueous liquid such as a syrup, an elixir, or an emulsion. An exemplary tablet formulation includes corn starch, lactose, and magnesium stearate as inactive ingredients. An exemplary syrup formulation includes citric acid, coloring dye, flavoring agent, hydroxypropylmethylcellulose, saccharin, sodium benzoate, sodium citrate and purified water.

For oral administration, the compounds can be formulated readily by combining the active peptides with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Peptide compositions may also contain one or more pharmaceutically acceptable carriers, which may include excipients such as stabilizers (to promote long term storage), emulsifiers, binding agents, thickening agents, salts, preservatives, solvents, dispersion media, coatings, antibacterial and antifungal agents, isotonic and absorption delaying agents, and the like. The use of such agents for pharmaceutically active compounds is well known in the art.

The compositions may conveniently be presented in unit dosage form and may be prepared by any of the methods well known in the art of pharmacy. Methods typically include the step of bringing the active ingredients of the invention into association with a carrier that constitutes one or more accessory ingredients.

Compositions of the present disclosure suitable for inhalation can be delivered as aerosols or solutions. An exemplary aerosol composition includes a peptide suspended in a mixture of trichloromonofluoromethane and dichlorodifluoromethane plus oleic acid. An exemplary solution composition includes a peptide dissolved or suspended in sterile saline (optionally about 5% v/v dimethylsulfoxide ("DMSO") for solubility), benzalkonium chloride, and sulfuric acid (to adjust pH).

Compositions of the present disclosure that are suitable for parenteral administration include sterile aqueous preparations of the peptides of the present disclosure and are typically isotonic with the blood of the patient to be treated. Aqueous preparations may be formulated according to known methods using those suitable dispersing or vetting agents and suspending agents. Sterile injectable preparations may also be sterile injectable solutions or suspensions in a non-toxic parenterally-acceptable diluent or solvent, for example as a solution in 1,3-butane diol. Among the acceptable vehicles and solvents that may be employed are water, Ringer's solution, and isotonic sodium chloride solution. In aqueous solutions, up to about 10% v/v DMSO or Trappsol can be used to maintain solubility of some peptides. Also, sterile, fixed oils may be conventionally employed as a solvent or suspending medium such as, for example, synthetic mono- or di-glycerides. In addition, fatty acids (such as oleic acid or neutral fatty acids) can be used in the preparation of injectibles. Further, Pluronic block copolymers can be formulated with lipids for time release from solid form over a period of weeks or months.

Compositions suitable for topical administration may be presented as a solution of the peptide in Trappsol or DMSO, or in a cream, ointment, or lotion. Typically, about 0.1 to about 2.5% active ingredient is incorporated into the base or carrier. An example of a cream formulation base includes purified water, petrolatum, benzyl alcohol, stearyl alcohol, propylene glycol, isopropyl myristate, polyoxyl 40 stearate, carbomer 934, sodium lauryl sulfate, acetate disodium, sodium hydroxide, and optionally DMSO. An example of an ointment formulation base includes white petrolatum and optionally mineral oil, sorbitan sesquioleate, and DMSO. An example of a lotion formulation base includes carbomer 940, propylene glycol, polysorbate 40, propylene glycol stearate, cholesterol and related sterols, isopropyl myristate, sorbitan palmitate, acetyl alcohol, triethanolamine, ascorbic acid, simethicone, and purified water.

Conjugated Anti-Heparan Sulfate and Anti-3-O Sulfated Heparan Sulfate Peptides for Intracellular Delivery of Therapeutic Compounds As part of the present disclosure, it was discovered that the heparan sulfate and 3-O sulfated heparan sulfate binding peptides, upon binding to HS and 3-OS HS, cross the plasma membrane and are transported into the cytoplasm and nucleus. Accordingly, the HS and 3-OS HS binding peptides described herein may be conjugated to one or more therapeutic compound to affect the intracellular and/or intranuclear delivery of the therapeutic compounds. Such conjugated HS and 3-OS HS peptides will find utility, for example, (1) in the preferential delivery of one or more compound(s) to an infected cell and/or (2) as a multivalent drug therapy wherein the HS and 3-OS HS peptide can (a) block viral infection (as described herein) and (b) cross the plasma membrane in an HS- and/or a 3-OS-dependent manner thereby delivering the compound(s) to affect intracellular and/or intranuclear clearance of virus-infected cells.

Nucleoside Analogs

A wide variety of therapeutic compounds can be conjugated to the HS and 3-OS HS binding peptides, which are described herein, to generate the presently disclosed therapeutic compound HS and 3-OS HS binding peptide conjugates. Exemplified herein are HS and 3-OS HS binding peptide conjugates that employ the guanosine analog acyclovir, or its prodrug valacyclovir, which can be metabolized and incorporated into the viral DNA within a virally infected cell. Acyclovir is depicted in the following Formula I:

Formula I

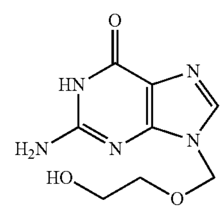

Acyclovir serves as a chain terminator for viral DNA synthesis and an inhibitor for viral DNA polymerase. Piret and Boivin, *Antimicrob. Agents Chemother.* 55(2):459-72 (2011). Acyclovir differs from other nucleoside analogues in that it contains a partial nucleoside structure wherein the sugar ring is replaced with an open-chain structure. Acyclovir is converted into acyclo-guanosine monophosphate by viral thymidine kinase. Cellular kinases subsequently convert the monophosphate form of acyclo-guanosine into acyclo-guanosine triphosphate, which is the high affinity substrate viral DNA polymerase. Because acyclovir has no 3' end, its incorporation into a nascent DNA strand results in its chain termination activity.

Acyclovir is active against a number of herpesvirus species, including herpes simplex virus type I (HSV-1), herpes simplex virus type II (HSV-2), and varicella zoster virus (VZV). Acyclovir is less active against Epstein-Barr virus (EBC) and cytomegalovirus (CMV).

Oligosaccharides

In addition to the use of nucleoside analogs, such as the guanosine analog acyclovir in generating HS and 3-OS HS binding peptide therapeutic compound conjugate, the present disclosure further contemplates conjugates that comprise one or more oligosaccharide such as a herpesvirus HS oligosaccharide. Exemplified herein are HS and 3-OS HS binding peptides that are conjugated to the HS octasaccharide 1 that has been shown to bind to the HSV-1 glycoprotein gD. Copeland et al., *Biochemistry* 47(21):5774-83 (2008) and Liu et al., *J. Biol. Chem.* 277(36):33456-67 (2002). HS octasaccharide 1 is presented herein by Formula II.

Formula II

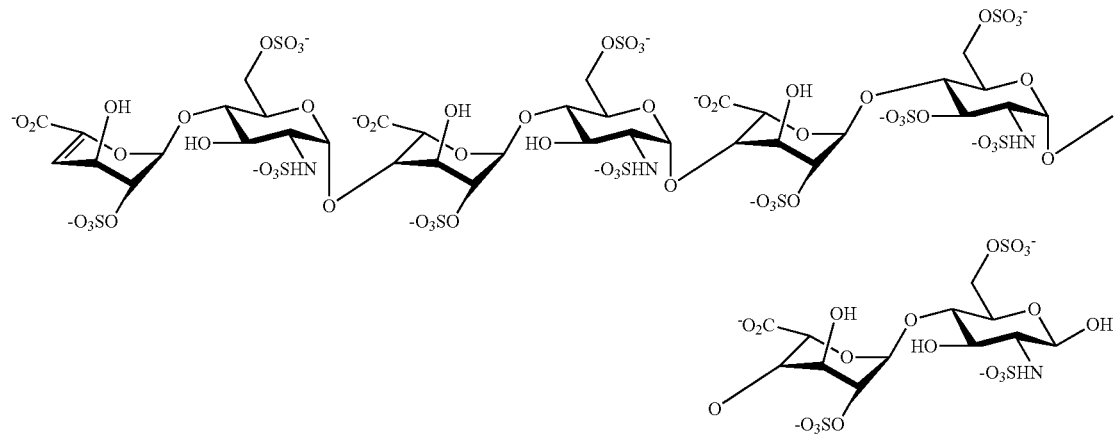

Other HS oligosaccharides, including HS octasaccharides, that are capable of binding to HSV-1 glycoproteins gB, gC, and gD can also be employed in the HS and 3-OS HS conjugates disclosed herein. HS structural elements that are critical to gB, gC, and gD binding can be identified by digesting heparan polysaccharides into oligosaccharides with heparan lyase. The resulting oligosaccharides can then be subjected to size exclusion chromatography to separate into tetrasaccharides, hexasaccharides, octasaccharides, and decasaccharides. Oligosaccharide fractions can be incubated with gB, gC, and/or gD and their binding affinities assessed using affinity co-electrophoresis. Oligosaccharide structures can be determined by immunoprecipitating gB-, gC-, and/or gD-oligosaccharide complexes, eluting bound oligosaccharides, and separating by anion exchange chromatography as described in Liu et al., *J. Biol. Chem.* 277(36):33456-67 (2002). The precise structure of an HS oligosaccharide having high gB, gC, and/or gD affinity can be determined through a combination of disaccharide compositional analysis and nanoelectrospray ionization (nESI) mass spectrophotometry. Pope et al., *Glycobiology* 11(6):505-13 (2001) and Liu et al., *J. Biol. Chem.* 285(44):34240-9 (2010).

Structurally well defined oligosaccharides can be synthesized by employing enzymatic synthetic methodology known in the art such as those described by Liu et al., *J. Biol. Chem.* 285(44):34240-9 (2010) and Linhardt et al., *Semin. Thromb. Hemost.* 33(5):453-65 (2007) and as presented in the following Synthetic Pathway I for HS oligosaccharides:

Synthetic Pathway I

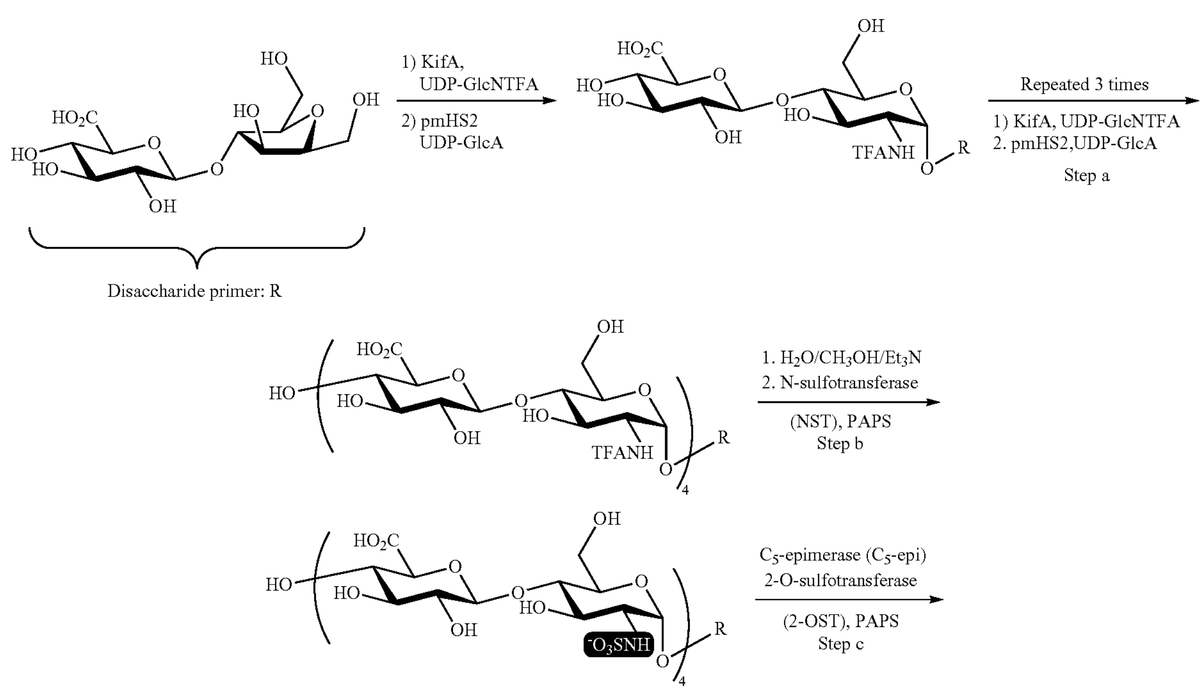

-continued

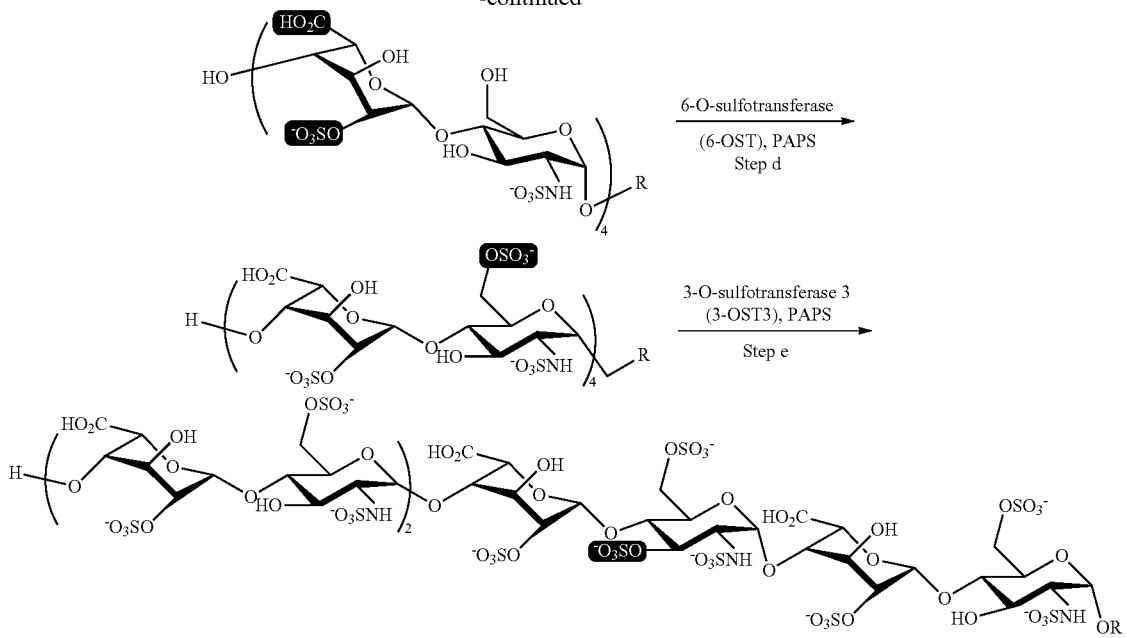

Starting from a disaccharide primer prepared from nitrous acid-degraded heparosan, backbone elongation can be achieved by altering KifA and pmHS2 treatment with UDP-GlcNTFA and UDP-GlcUA as donor substrates, which can be followed by modification with specific sulfotransferases. To generate different HS sequences, the enzymatic steps can be varied. For example, the $C_5$-epi can be removed and 2-O sulfotransferase R189A mutant can be used for step c of the synthetic pathway shown above. Unlike wild type 2-OST, 2-OST R189A specifically sulfates the GlcUA, not IdoUA. Bethea et al., *Proc. Natl. Acad. Sci. U.S.A.* 105(48):18724-9 (2008). As a result, the desired octasaccharide can have GlcUA2S instead of the IdoUA2S units. Similar enzymatic variations including HS oligosaccharides prepared without 6-O-sulfation by skipping the 6-O sulfotransferase (6-OST) treatment step (step d) will yield a number of unique octasaccharides for the generation of HS and 3OS HS binding peptide conjugates. Suitable oligosaccharides, including octasaccharides, can be tested for their ability to inhibit multiple steps during a viral lifecycle, such as a herpesvirus lifecycle (e.g., HSV-1). Attachment inhibition can be determined by a flow cytometry binding assay. O'Donnell et al., *Virology* 397(2):389-98 (2010). Green HSV-1 (K26GFP) can be tested for binding to HeLa cells at 4° C. to prevent penetration. HeLa cells can be preincubated with an octasaccharide or control followed by the addition of green virus. Unbound virions are washed away and flow cytometry performed to quantify the presence of a green signal on a cell. Desai and Person, *J. Virol.* 72(9):7563-8 (1998).

Small Molecules

The present disclosure further contemplates HS and 3OS HS binding peptides that are conjugated to one or more small molecule(s). Small molecule inhibitors are well known, as exemplified by the HS binding small molecule Bis-2-methyl-4-amino-quinolyl-6-carbamide (Surfen; see Formula III), and can be readily identified by methodology that is known in the art.

Formula III

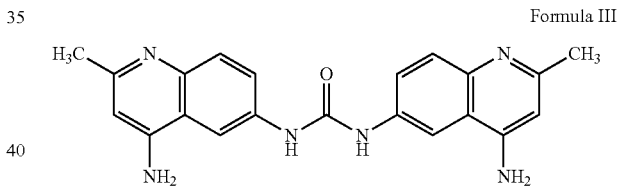

For example, robotic screening of small molecule libraries can be performed to identify new inhibitors of HSV-1 gB, gC, and/or gD functions. Baculovirus-expressed gB, gC, and/or gD can be affinity purified and screened against one or more drug-like small molecule libraries that provide: (1) diversity screening compounds; (2) kinase targeted compounds; and (3) LOPAC (Library of Pharmaceutically Active Compounds). Cytotoxicity of the hit compounds can be tested as described in Bacsa et al., *J. Gen. Virol.* 92(Pt 4):733-43 (2011). Potential gB, gC, and/or gD binders/inhibitors can be analyzed by surface SPR and/or Bioforte OCTET for affinity determinations as described in Tong et al., *Cell Res.* (in press) (2011) and Abdiche et al., *Anal. Biochem.* 411(1):139-51 (2011).

Coupling of Therapeutic Compounds to HS and 3-OS HS Binding Peptides

HS and 3-OS HS binding peptides can be coupled to one or more therapeutic compound to generate HS and 3-OS HS binding peptide-therapeutic compound conjugates by methodology that is well known to those of skill in the art.

HS and 3-OS HS binding peptides can be coupled to HS oligosaccharides to generate glycopeptides having enhanced affinity through a multivalent effect through the binding to multiple viral surface molecules, such as herpesvirus surface molecules. Peptides can be linked to HS oligosaccharides via hydrazide/aldehyde chemistry as presented in the following Synthetic Pathway II:

Synthetic Pathway II a)

H₂N—[resin] →(Multiple rounds of solid phase synthesis)→ H₂N—LIRSRKNPIISR—[resin] with protections ᵗBu, Boc, ᵗBu, Pbf, Trt, Pbf Fully protected peptide 9 on resin 1) Boc-HNN-CH₂-(O-Linker)ₙ-O-CH₂-COOH (Acid 17)
2) Cleavage from resin and global deprotection with acid H₂NHN—LIRSRKNPIISR
↑ Linker 1) HS Oligo—CHO
2) NACNBH₃ reduction → HNHN—LIRSRKNPIISR with HS Oligo Glycopeptide 18 with its N-terminal linked with an HS oligosaccharide b)

H₂N—LIRSRKNPIISR—[resin] with ᵗBu, Boc, ᵗBu, Pbf, Trt, Pbf

Fully protected peptide 9 on resin

1) N-terminal capping and mild acid cleavage from resin
2) Boc-HNN-CH₂-(O-Linker Amine 19)ₙ-O-CH₂-CH₂-NH₂
3) TFA deprotection → LIRSRKNPIISR—NHNH₂
↑ Linker C-terminal functionalized HSV-1 binding peptide Both C- and N-terminal hydrazide functionalization of the peptides can be employed to achieve optimal linkage. Carboxylic acid 17 is added to functionalize the peptide's N-terminus. Upon cleavage from the resin and global deprotection, the peptide with N-terminal hydrazide is obtained, which can undergo chemoselective ligation reaction with an aldehyde functionalized HS oligosaccharide followed by reduction to generate a glycopeptides 18. Alternatively, the peptide can be functionalized at its C-terminus with amine 19 to introduce a hydrazide moiety, which can subsequently be coupled with HS oligosaccharide to form a glycopeptides in a similar manner as the formation of 18. HS and/or 3OS HS binding peptide-oligosaccharide conjugates can, optionally, employ a linker of varying length to optimize binding affinity. The binding of a multivalent glycopeptides to a virion can be determined by using a Bioforte OCTET system as described in Abdiche et al., *Anal. Biochem.* 411(1):139-51 (2011).

HS and 3-OS HS binding peptides can be coupled to one or more nucleoside analog by methodology that known in the art. For example, acyclovir can be modified with an HS or a 3-OS HS binding peptide by esterification of acyclovir with a protected peptide followed by acid promoted deprotection as presented in the following Synthetic Pathway III:

Synthetic Pathway III

Protected peptide—CO₂H
1) EDCl, NHS
2) H₂N—Linker—CO₂H
→ Protected peptide—Linker—CO₂H 1) EDCl, DMAP, acyclovir
2) TFA (peptide deprotection)

-continued peptide—Linker—●← acyclovir

HS-target peptide acyclovir conjugate

Acyclovir has been shown to be stable under peptide deprotection conditions. Friedrichsen et al., *Eur. J. Pharm. Sci.* 16(1-2):1-13 (2002). The attachment of a therapeutic compound to an HS and 3-OS HS binding peptide will significantly enhance the cellular uptake of the therapeutic compound. Once inside a cell, the intracellular carboxyl esterases cleave the ester linkage thereby releasing the therapeutic compound. De Clercq and Field, *Br. J. Pharmacol.* 147(1):1-11 (2006). Depending upon the precise application contemplated, and the nature of the therapeutic compound, a linker may be employed between the HS and 3-OS HS binding peptide and the therapeutic compound.

Methods for Blocking Viral Binding to and Viral Infection of a Target Cell and for Treating Virus-Mediated Disease in a Patient In addition to the above-described Group 1, retro-inverso Group 1, Group 2, and retro-inverso Group 2 peptides, and compositions thereof, the present disclosure also provides methods for blocking the binding of a virus to a target cell and/or the infection of a target cell by a virus. In various embodiments, such methods include contacting a target cell, either in vitro or in vivo, with a Group 1 peptide, a retro-inverso Group 1 peptide, a Group 2 peptide, and/or a retro-inverso Group 2 peptide.

In some embodiments, methods for blocking the binding or infection of a target cell by a virus may include contacting the target cell with a peptide that comprises at least 10 or at least 12 consecutive amino acids of the sequences (SEQ ID NO: 2)
XRXRXKXXRXRX
and (SEQ ID NO: 4)
XXRRRRXRRRXK.

In other embodiments, the target cell may be contacted with a peptide that comprises at least 10 or at least 12 consecutive amino acids of the sequence LRSRTKIIRIRH (SEQ ID NO: 1) and/or at least 10 or at least 12 consecutive amino acids of the sequence MPRRRRIRRRQK (SEQ ID NO: 3). Optionally, the peptide may include one or more D-amino acids.

In other embodiments, methods for blocking the binding or infection of a target cell by a virus may include contacting the target cell with a peptide that comprises at least 10 or at least 12 consecutive amino acids of the sequences XRX RXXKXRXRX (SEQ ID NO: 8), wherein at least one amino acid is a D-amino acid, and (SEQ ID NO: 10)
KXRRRXRRRRXX, wherein at least one amino acid is a D-amino acid. It is further contemplated that by these methods, a target cell is contacted, either in vitro or in vivo, with a retro-inverso Group 1 and/or a retro-inverso Group 2 peptide that comprises at least 10 or at least 12 consecutive amino acids of the sequences XRXRXXKXRXRX (SEQ ID NO: 8), wherein all the amino acids are D-amino acids, and (SEQ ID NO: 10)
KXRRRXRRRRXX, wherein all the amino acids are D-amino acids.

Within certain aspects of these methods, the target cell can be contacted with a peptide that comprises at least 10 or at least 12 consecutive amino acids of the sequence HRIRIIKTRSRL (SEQ ID NO: 7), wherein at least one amino acid is a D-amino acid, and/or at least 10 or at least 12 consecutive amino acids of the sequence KQRRRIRRRRPM (SEQ ID NO: 9), wherein at least one amino acid is a D-amino acid. Within further aspects of these methods, the target cell can be contacted with a peptide that comprises at least 10 or at least 12 consecutive amino acids of the sequence HRIRIIKTRSRL (SEQ ID NO: 7), wherein all the amino acids are D-amino acids, and/or at least 10 or at least 12 consecutive amino acids of the sequence KQRRRIRRRRPM (SEQ ID NO: 9), wherein all the amino acids are D-amino acids.

Also disclosed herein are methods for the treatment of a patient who is either infected with a virus or who is susceptible to a viral infection. By these methods, a Group 1 and/or a Group 2 peptide that comprises at least 10 or at least 12 consecutive amino acids of the sequences (SEQ ID NO: 2)
XRXRXKXXRXRX
and (SEQ ID NO: 4)
XXRRRRXRRRXK is administered to a patient subsequent or prior to exposure and/or infection with a virus, such as a herpesvirus (e.g., an α-herpesvirus, a β-herpesvirus, and/or a γ-herpesvirus). Within certain aspects, the α-herpesvirus is HSV-1. Within other aspects, the β-herpesvirus is cytomegalovirus (CMV). Within yet other aspects, the γ-herpesvirus is human herpesvirus-8 (HHV-8).

Also disclosed herein are methods for the treatment of a patient who is either infected with a virus or is susceptible to a viral infection. By these methods, a retro-inverso Group 1 and/or a retro-inverso Group 2 peptide that comprises at least 10 or at least 12 consecutive amino acids of the sequences XRXRXXKXRXRX (SEQ ID NO: 8), wherein at least one amino acid is a D-amino acid, and (SEQ ID NO: 10)
KXRRRXRRRRXX, wherein at least one amino acid is a D-amino acid, is administered to a patient subsequent or prior to exposure and/or infection with a virus, such as a herpesvirus (e.g., an α-herpesvirus, a β-herpesvirus, and/or a γ-herpesvirus). It is further contemplated by these methods, a retro-inverso Group 1 and/or a retro-inverso Group 2 peptide that comprises at least 10 or at least 12 consecutive amino acids of the sequences XRXRXXKXRXRX (SEQ ID NO: 8), wherein all the amino acids are D-amino acids, and (SEQ ID NO: 10)
KXRRRXRRRRXX, wherein all the amino acids are D-amino acids, is administered to a patient subsequent or prior to exposure and/or infection with a virus, such as a herpesvirus (e.g., an α-herpesvirus, a β-herpesvirus, and/or a γ-herpesvirus). Within certain aspects, the α-herpesvirus is HSV-1. Within other aspects, the β-herpesvirus is cytomegalovirus (CMV). Within yet other aspects, the γ-herpesvirus is human herpesvirus-8 (HHV-8).

Within certain aspects of these methods, a peptide that comprises at least 10 or at least 12 consecutive amino acids of the sequence LRSRTKIIRIRH (SEQ ID NO: 1) and/or at least 10 or at least 12 consecutive amino acids of the sequence MPRRRRIRRRQK (SEQ ID NO: 3) can be administered to the patient.

Within certain aspects of these methods, a peptide that comprises at least 10 or at least 12 consecutive amino acids of the sequence HRIRIIKTRSRL (SEQ ID NO: 7), wherein at least one amino acid is a D-amino acid, and/or at least 10 or at least 12 consecutive amino acids of the sequence KQRRRIRRRRPM (SEQ ID NO: 9), wherein at least one amino acid is a D-amino acid, can be administered to the patient. Within further aspects of these methods, a peptide that comprises at least 10 or at least 12 consecutive amino acids of the sequence HRIRIIKTRSRL (SEQ ID NO: 7), wherein all the amino acids are D-amino acids, and/or at least 10 or at least 12 consecutive amino acids of the sequence KQRRRIRRRRPM (SEQ ID NO: 9), wherein all the amino acids are D-amino acids, can be administered to the patient.

As shown herein, the in vivo administration of a G1 and/or G2 a peptide(s) prevents HSV-1 spread in the cornea. These findings highlight the in vivo significance of HS and 3OS HS during viral infection, such as during an ocular herpes infection. Thus, G1, riG1, G2 and riG2 represent exemplary 12-mer peptides that exhibit a unique ability to bind to critical domains within HS and/or 3OS HS, respectively, which domains are believed to be required for viral entry. Thus, the peptides presented herein will find broad application methods for the treatment of diseases associated with HS and/or 3OS HS-mediated viral infections, such as herpesvirus infections.

Suitable routes of in vivo administration may, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections. Alternately, peptide compositions may be administered in a local rather than a systemic manner such as, for example, via injection of the preparation directly into a specific region of a patient's body.

More specifically, a therapeutically effective amount means an amount of active ingredients effective to prevent, alleviate or ameliorate symptoms of disease or prolong the survival of the subject being treated. Determination of a therapeutically effective amount is well within the capability of those skilled in the art.

For any peptide composition used in the methods of the present disclosure, the therapeutically effective amount and toxicity can be estimated initially from in vitro assays and cell culture assays. A suitable dose can be determined in animal models and such information can be used to more accurately determine useful doses in humans.

Toxicity and therapeutic efficacy of the peptides described herein can be determined by standard pharmaceutical procedures in vitro, in cell cultures, and/or in experimental animal models. The data obtained from these in vitro and cell culture assays and animal studies can be used in formulating a range of dosage for use in a human patient. The dosage may vary depending upon the dosage form employed and the route of administration utilized. The exact formulation, route of administration, and dosage can be chosen by the individual physician in view of the patient's condition. See, e.g., Fingl et al., "The Pharmacological Basis of Therapeutics", Ch. 1 p. 1 (1975).

Depending on the severity and responsiveness of the viral infection to be treated, dosing can be of a single or a plurality of administrations, with course of treatment lasting from several days to several weeks or until cure is effected or diminution of the viral infection is achieved. The amount of a peptide composition to be administered will depend upon the patient being treated, the severity of the affliction, the manner of administration, and the judgment of the prescribing physician.

Doses of the pharmaceutical compositions will vary depending upon the patient and upon the particular route of administration used. Dosages can range from 0.1 to 100,000 µg/kg a day, more typically from 1 to 10,000 µg/kg or from 1 to 100 µg/kg of body weight or from 1 to 10 µg/kg. Doses are typically administered from once a day to every 4-6 hours depending on the severity of the condition. For acute conditions, it is preferred to administer the peptide every 4-6 hours. For maintenance or therapeutic use, it may be preferred to administer only once or twice a day. Preferably, from about 0.18 to about 16 mg of peptide are administered per day, depending upon the route of administration and the severity of the condition. Desired time intervals for delivery of multiple doses of a particular composition can be determined by one of ordinary skill in the art employing no more than routine experimentation.

All patents, patent application publications, and patent applications, whether U.S. or foreign, and all non-patent publications referred to in this specification are expressly incorporated herein by reference in their entirety.

EXAMPLES

Example 1

Experimental Procedures

Selection of Phages Against HS and 3-OS HS by Library Panning

A phage display library (PhD,™-12) expressing 12-mer peptides fused to a minor coat protein (pIII) of a non-lytic bacteriophage (M13) was purchased from New England Biolabs (Cambridge, Mass.). A purified form of HS isolated from bovine kidney was purchased from Sigma. Soluble 3OS HS modified by 3-OST-3 was prepared as previously described. Tiwari et al., *J. Gen. Virol.* 88:1075-1079 (2007).

Screening of the phage display library was accomplished by an affinity selection (or bio-panning) process during which phage populations were selected for their ability to bind HS and 3OS HS (modified by 3-OST-3). Both targets at a concentration of 10 µg/ml were used for overnight coating of wells of 96 well plates (Nalge Nunc International, Naperville, Ill.) in a humidifier chamber at 4° C. The following day, the plates were blocked for 1 hr at room temperature with 5 mg/ml bovine serum albumin (BSA) in 0.1M $NaHCO_3$ (pH 8.6) buffer. The plates were then washed six times with TBST (50 mM Tris-HCl, pH 7.5, 150 mM NaCl, 0.1% [vol/vol] Tween-20). The phage library was added to the plate at a concentration of $2\times10^{11}$ in 100 µl in TBST. The plate was gently rocked for 1 hr at room temperature. Unbound phages were removed by washing plates 10 times with 1 ml of TBST. Bound phages were eluted by adding 100 µl of Tris-HCl at pH 3.0. The eluate containing bound phages was removed and the phages were amplified in *Escherichia coli* ER2738 bacteria and partially purified by polyethylene glycol (PEG) precipitation. The binding, elution, and amplification steps were repeated using HS and 3-OST-3 modified HS as targets. Three rounds of selection were carried out to select for binders of progressively higher specificity. Low concentrations of detergent (Tween-20) in the early rounds resulted in high eluate titers, and the stringency was gradually increased with each successive round by raising Tween-20 concentration stepwise to a maximum of 0.5%. This allowed selection of high affinity binding phages. For final selection, the eluted phages were plaque purified and titered on soft-agar plates.

Nucleotide Sequencing and Analysis

Automated nucleotide sequencing was performed to determine the sequences of the peptides encoded by the phages (Research Resource Center (RRC), University of Illinois at Chicago). Phage DNA was purified according to the manufacture's protocol using QIAGEN mini-prep kit (Valencia, Calif.). DNA sequencing was initiated using ABI prism BigDye Terminator Kit (Applied Biosystem, Foster City, Calif.) and the −96 gIII sequencing primer (New England Biolabs, Cambridge, Mass.). Sequencing was performed on a Hitachi 3100 gene analyzer (Applied Biosystems, Foster City, Calif.) and the 36 nucleotide long DNA regions encoding the 12-mer peptides were identified and used for peptide synthesis. The synthetic peptides were resuspended at a concentration of 10 mM in phosphate buffer saline (PBS) at pH 7.4, and stored at −80° C. until use.

The purity of the peptides was >95% as verified by high-performance liquid chromatography. The correct mass of the peptides was confirmed by mass spectrometry.

Cell Culture and Viruses

The presently described examples employed a variety of cell types, including wild-type Chinese hamster ovarian (CHO-K1), mutant CHO-745, and CHO-Iβ8 cells. In addition, primary cultures of human corneal fibroblasts (CF), retinal pigment epithelial (RPE), human conjunctival (HCjE), Vero, and HeLa cells were also used.

CHO cell lines were grown in Ham's F-12 medium (Gibco/BRL, Carlsbad, Calif., USA) supplemented with 10% fetal bovine serum (FBS), penicillin, and streptomycin (P/S) (Gibco/BRL). CF, HeLa, and RPE cells were grown in Dulbecco's Modified Eagle Medium (DMEM) supplemented with 10% FBS and P/S (Tiwari et al., *J. Virol.* 80:8970-8980 (2006) and Tiwari et al., *FEBS J.* 275:5272-5285 (2008)), and Vero cells were grown in DMEM with 5% FBS and P/S. Cultured HCjE cells were grown as described in Akhtar et al., *Invest. Ophthalmol. Vis. Sci.* 49:4026-4035 (2008).

HSV-1 strains, including the β-galactasidase expressing recombinant HSV-1 (KOS) gL86 virus strain, the HSV-2 G strain, and the HfM, F, MP and KOS strains were provided by P. G. Spear at Northwestern University. Oh et al., *Biochem Biophys Res Commun* 391, 176-81 (2010). Green fluorescent protein (GFP) expressing HSV-1 (K26GFP), GFP expressing HHV-8 were provided by Drs. Prashant Desai at Johns Hopkins University and J. Viera at University of Washington. Desai and Person, *J. Virol.* 72:7563-7568 (1998). The β-galactasidase-expressing recombinant cytomegalovirus (CMV) was obtained from ATCC.

HSV-1 Entry Assay

HSV-1 entry was assayed as described in Shukla et al., *Cell* 99:13-22 (1999). CHO-K1 cells were grown in 6-well plates to subconfluence and then transfected with 2.5 µg of expression plasmids for gD receptors nectin-1 (pBG38), HVEM (pBec10), 3-OST-3 isoform (pDS43), or pCDNA3.1 (empty vector) using LipofectAMINE (Gibco/BRL). At 16 h post-transfection, the cells were replated into 96-well dishes for pre-incubation with peptides at different concentrations for 60 min at room temperature. In parallel, natural target cells (HeLa, CF, and RPE) were also pre-treated with the peptides for the same duration. In all cases, unbound peptides were removed after washing 3× with PBS. Thereafter, cells were infected for 6 h with a recombinant virus, HSV-1 (KOS) gL86, at multiple plaque forming units (PFUs) and β-galactosidase assays were performed using either a soluble substrate o-nitrophenyl-β-D-galactopyranoside (ONPG at 3.0 mg/ml; ImmunoPure, Pierce) or X-gal (Sigma). For the soluble substrate, the enzymatic activity was measured at 410 nm using a micro-plate reader (Spectra Max 190, Molecular Devices, Sunnyvale, Calif.). For the X-gal assay, cells were fixed (2% formaldehyde and 0.2% glutaradehyde) and permeabilized (2 mM $MgCl_2$, 0.01% deoxycholate, and 0.02% nonidet NP-40 (Sigma)). 1 ml of β-galactosidase reagent (1.0 mg/ml X-gal in ferricyanide buffer) was added to each well and incubated at 37° C. for 90 min before the cells were examined using bright field microscopy under the 20× objectives of the inverted microscope (Zeiss Axiovert 100 M).

Fluorescent Microscopy of Viral Entry

Cultured monolayers of HeLa and CF (approximately $10^6$ cells/well) were grown overnight in DMEM media containing 10% FBS on chamber slides (Lab-Tek). One pool of each cell-type was pre-treated with G1, G2, or a control peptide for 60 min. Cells were then infected with HSV-1 K26GFP (Desai and Person *J. Virol.* 72:7563-7568 (1998)) at 50 PFU in serum-free media OptiMEM (Invitrogen), which was followed by fixation of cells at 90 min post-infection using fixative buffer (2% formaldehyde and 0.2% glutaradehyde). The cells were then washed and permeabilized with 2 mM $MgCl_2$, 0.01% deoxycholate, and 0.02% Nonidet NP-40 for 20 min. After rinsing, 10 nM rhodamine-conjugated phalloidin (Invitrogen) was added for F-actin staining at room temperature for 45 min. The cells were washed and the images of labeled cells were acquired using a confocal microscope (Leica, Solms, Germany) and analyzed with MetaMorph software (Molecular Devices, Sunnyvale, Calif.).

CMV Entry Assay

Natural target RPE cells were incubated with G1 and G2 peptides for 60 min at room temperature before the cells were infected with β-galactosidase expressing CMV (ATCC) for 8 h. β-galactosidase assays were performed using either a soluble substrate o-nitrophenyl-β-D-galactopyranoside (ONPG at 3.0 mg/ml; ImmunoPure, Pierce) or X-gal (Sigma).

HHV-8 Infection Assay

HCjE cells grown in chamber slides (Labteck) or in a 96 well plate were pre-treated with G1, G2, or control peptides for 60 min at room temperature followed by inoculation with recombinant rHHV-8.152, expressing the green fluorescent protein (GFP). Viera et al., *J. Virol.* 72:5182-5188 (2000). 48-hr post-infection, GFP-positive cells were visualized under microscope (Zeiss Axioverst 100M). HHV-8 infection was determined as relative fluorescence units (RFU) using GENios Pro plate reader (TECAN) at 480-nm excitation and 520-nm emission frequencies. Five measurements of negative control, positive control, and the test samples were performed. Data were expressed as mean±SD.

HSV-1 Glycoprotein Induced Cell-to-Cell Fusion Assay

CHO-K1 "effector" cells (grown in F-12 Ham, Invitrogen) were co-transfected with plasmids expressing four HSV-1(KOS) glycoproteins: pPEP98 (gB), pPEP99 (gD), pPEP100 (gH), and pPEP101 (gL), along with the plasmid pT7EMCLuc that expresses firefly luciferase gene under transcriptional control of the T7 promoter. Pertel et al., *Virology* 279:313-324 (2001). Wild-type CHO-K1 cells, which express cell-surface HS but lack functional gD receptors, were transiently transfected with HSV-1 entry receptors. Wild-type CHO-K1 cultured cells expressing HSV-1 entry receptors or naturally susceptible cells (human CF) considered as "target cells" were co-transfected with pCAGT7 that expresses T7 RNA polymerase using chicken actin promoter and CMV enhancer. Tiwari et al., *FEBS Letters* 581:4468-4472 (2007). Untreated effector cells expressing pT7EMCLuc and HSV-1 essential glycoproteins, and target cells expressing gD receptors transfected with T7 RNA polymerase, were used as positive controls. G2 or control peptide-treated target cells were then co-cultivated (1:1 ratio) for 18 h with effector cells for fusion. Activation of a reporter luciferase gene—as a measure of cell fusion—was examined using reporter lysis assay (Promega) at 24 hr post mixing.

Flow Cytometry Analysis

Flow cytometry was performed to detect the effect of G2 peptide on GFP-HSV-1 binding to human CF. Monolayers of approximately $5 \times 10^6$ CF were pre-treated with G2 peptide for 60 min followed by incubation with GFP-expressing HSV-1 (K26GFP) at 4° C. A control peptide treated and untreated cells were similarly incubated with HSV-1 GFP virions. Uninfected CF were used as background negative control. GFP expression from the viral capsid on cell surface was examined by a flowcytometer (MoFlo).

Immunohistochemistry

BALB/c mice with pre-scarred corneal upper surface were treated with PBS-based eye drops containing 0.5 mM G1, G2, or control peptide followed by inoculation of HSV-1 (KOS). Mice were sacrificed after 4 and 7 days for HSV-1 detection. Immunohistochemistry was performed as described by Akhtar et al., *Invest. Ophthalmol. Vis. Sci.* 49:4026-4035 (2008). Briefly, tissue sections were hydrated with distilled water and antigen retrieval was performed using DAKO Target Retrieval Solution 10× concentrate (DAKO, Carpinteria, Calif.). Nonspecific staining was blocked using $H_2O_2$ solution for 10 minutes followed by a protein block for 10 minutes. Sections were incubated with HSV-1 gD specific antiserum (1:100 dilution) at room temperature for 1 hr followed by a 40-minute incubation with the secondary antibody (HRP-conjugated goat anti-rabbit IgG, 1:500; Sigma, St. Louis, Mo.). Expression of gD was detected using the DAKO Envision$^+$ kit. Confocal and differential interference contrast (DIC) image acquisition was conducted with an SB2-AOBS confocal microscope (Leica, Solms, Germany).

Statistics

The data presented herein are means±SD of triplicate measures of three or more experiments each performed independently. Error bars represent one standard deviation (SD). Statistical significance was calculated using Student's t-test. A p-value <0.05 was considered statistically significant.

Example 2

Identification of HS and 3-OS HS Binding Peptides that Block HSV-1 Entry

Three rounds of screening of phages from a 12-mer peptide phage display library resulted in the enrichment of phages that specifically-bound to HS and/or to 3-OS HS. Peptide sequences from individual plaques were deduced by determining the nucleotide sequences of the portion of the phage genome that encoded them. The predicted peptide sequences of about 200 plaques were determined and sorted into two groups on the basis of their targets. A frequently repeating peptide sequence from each group was subsequently selected for further characterization. The two most frequently isolated peptide sequences LRSRTKIIRIRH (designated G1 for HS binding group 1) and MPRRRRIR-RRQK (designated G2 for 3-OS HS binding group 2) were synthesized and examined for each peptide's ability to inhibit HSV-1 infection of 3-OST-3 (FIG. 1A), nectin-1 (FIG. 1B), and HVEM (FIG. 1C) expressing CHO-K1 cells. Cells were pre-incubated with G1, G2, or control peptide (Cp) at indicated concentration in mM or mock treated (C) with 1× phosphate saline buffer for 60 min at room temperature. After 60 min, a β-galactosidase-expressing recombinant virus HSV-1 (KOS) HSV-1 gL86 (25 pfu/cell) virus was used for infection. After 6 hr, the cells were washed, permeabilized, and incubated with ONPG substrate (3.0 mg/ml) for quantitation of β-galactosidase activity expressed from the input viral genome. The enzymatic activity was measured at an optical density of 410 nm ($OD_{410}$). Each value shown is the mean of three or more determinations (±SD).

Both of the G1 and G2 peptides were able to block HSV-1 entry into CHO-K1 cells expressing one of the three gD receptors (i.e., 3-OS HS, nectin-1, and HVEM). Viral entry blockage occurred in a dose-dependent manner and was independent of gD receptor used. The concentration of each peptide that produced 50% of its maximum potential inhibitory effect ($IC_{50}$) ranged from 0.02 to 0.03 mM. A control phage bearing the sequence RVCGSIGKEVLG (designated Cp) did not inhibit HSV-1 entry. None of the peptides exhibited significant cytotoxicity (MTS assay, Promega) at <5 mM. The highest concentration of peptides in the experiments presented herein was 0.5 mM.

Figure 2:
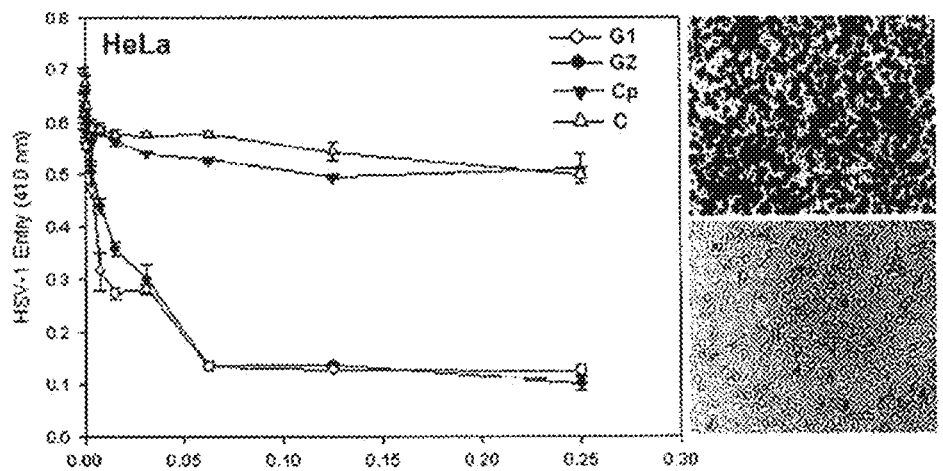
FIG. 2 demonstrates that G1 and G2 peptides block HSV-1 entry into human target cells.
Figure 2:
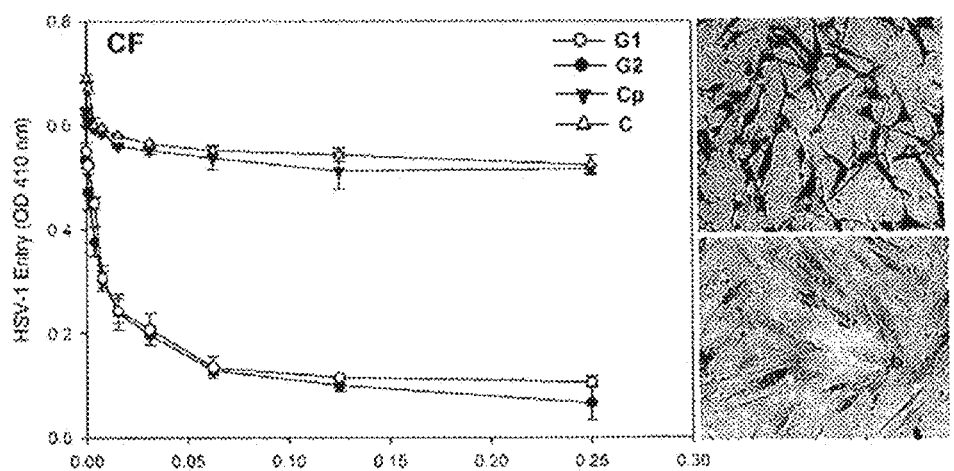

The ability of the G1 and G2 peptides to block HSV-1 entry into natural target cells (HeLa and primary cultures of human CF) was compared. A similar dosage response curve was generated when HeLa (FIG. 2A) or CF (FIG. 2B) were pre-treated with G1 or G2 peptides during HSV-1 entry. The control peptide treated cells had no effect on HSV-1 entry (FIG. 2). HeLa cells (FIG. 2A) and primary cultures of human corneal fibroblasts (CF) (FIG. 2B) were tested. Cells in 96-well plates were pre-treated for 60 min with indicated mM concentrations of G1, G2, or Cp peptides. Mock-treated cells (abbreviated as C) served as a control. Pretreated cells were infected with a β galactosidase-expressing recombinant virus HSV-1 (KOS) HSV-1 gL86 (25 pfu/cell) for 6 hr. Viral entry was quantitated as described above in reference to FIG. 1. Confirmation of HSV-1 entry blocking activity of G1, G2, and control (Cp) peptides on a per cell basis was obtained after cells were infected as described above followed by X-gal (1.0 mg/ml) staining (Right panels), which yields an insoluble blue product upon hydrolysis by β-galactosidase expressed from the input viral genomes. Dark (blue) cells represent infected cells, uninfected cells do not show any color. Microscopy was performed using a 20× objective of Zeiss Axiovert 100.

Use of insoluble blue cell assay (X-gal as the substrate for β-galactosidase) further confirmed that the peptides were effective in blocking infection of individual cells (FIGS. 2A and 2B, right panels). In virtually all cases, G2 peptide was slightly more effective in blocking entry than G1.

Example 3

The Peptide Inhibitors are Also Active Against a Variety of HSV-1 Strains

This Example demonstrates that the inhibitory effect of the G2 peptide is not limited by viral strain or serotype.

Figure 3:
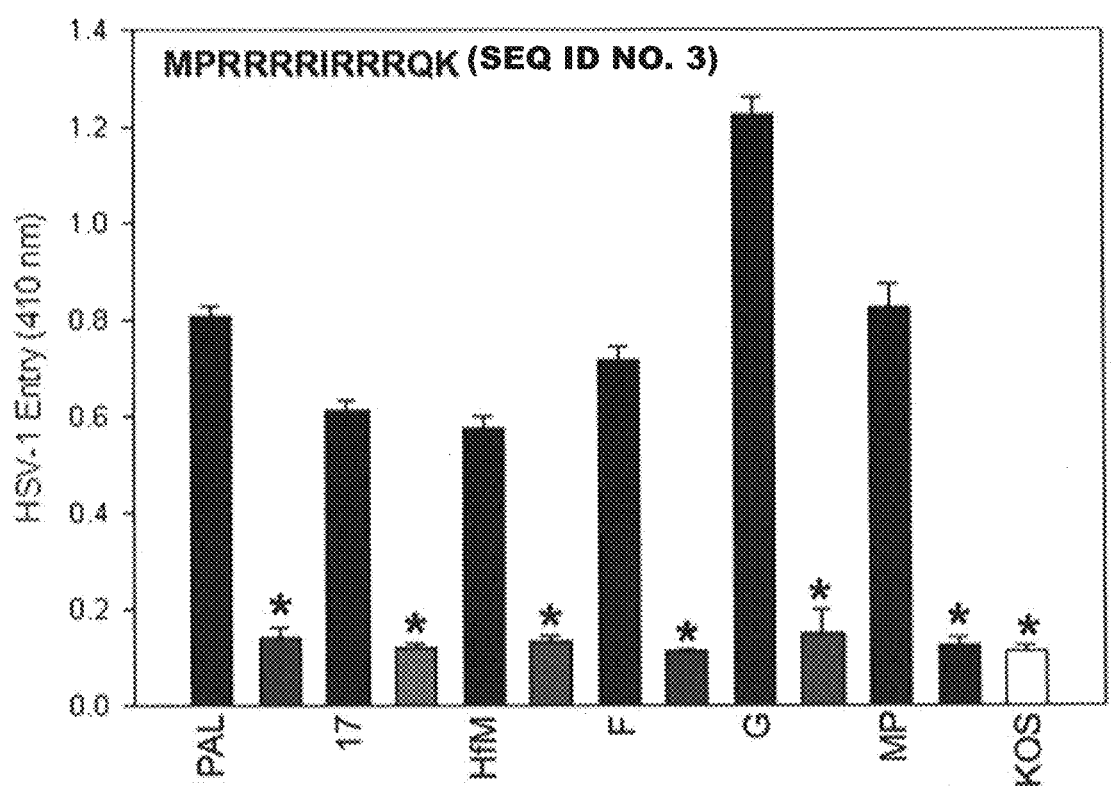
FIG. 3 demonstrates that HSV-1 entry blocking activity of G2 peptide is not HSV-1 strain specific.

The anti-HSV properties of the G1 and G2 peptides were evaluated against common strains of HSV-1 and HSV-2 (i.e., strains F, G, Hfem, MP, KOS, and 17). Dean et al., *Virology* 199:67-80 (1994). 3-OST-3 expressing CHO Ig8 reporter cells were used that express β-galactosidase upon viral entry. Montgomery et al., *Cell* 87:427-436 (1996). Cells were pre-incubated with G1, G2, or control peptide (Cp) and subsequently infected with the viruses. G2 or Cp control at 0.5 mM concentration was incubated for 60 min at room temperature with a reporter CHO-Ig8 cells that express β-galactosidase upon HSV-1 entry. After incubation, the cells were infected with HSV-1 (Pal, 17, Hfm, F, KOS, and MP) and HSV-2 (G) strains at 25 pfu/cell for 6 hr at 37° C. Blockage of viral entry was measured by ONPG assay as described in Example 2 and as presented in FIG. 1. These results, which are presented in FIG. 3, demonstrated that G1 and G2 blocked entry of various HSV-1 strains by 70-80% at 0.5 mM concentration.

Example 4

Structural Aspects of G1 and G2 Peptides G2 Shows More Dependence on Charged Residues To better understand the inhibitory potential of G1 and G2 peptides, synthetic short variants (10-mer) were synthesized that lacked the terminal non-positively charged amino acids.

In case of G1, N-terminus L and C-terminus H residues were removed. For G2, the N-terminus flanking residues (M and P) were removed. Without being bound by theory, it is believed that 12-mer peptides are too short to adopt substantial secondary or tertiary structures and that the primary structure of those peptides, which includes a defined sequence or groupings of positively charged residues, plays a critical role in mediating inhibition of HSV-1 entry. Synthetic 10-mer versions of G1 and G2 (shown above) were tested for blocking HSV-1(KOS)gL86 entry into cultured CF. After 6 h, the viral entry was measured by ONPG assay as described in FIG. 1.

Figure 4:
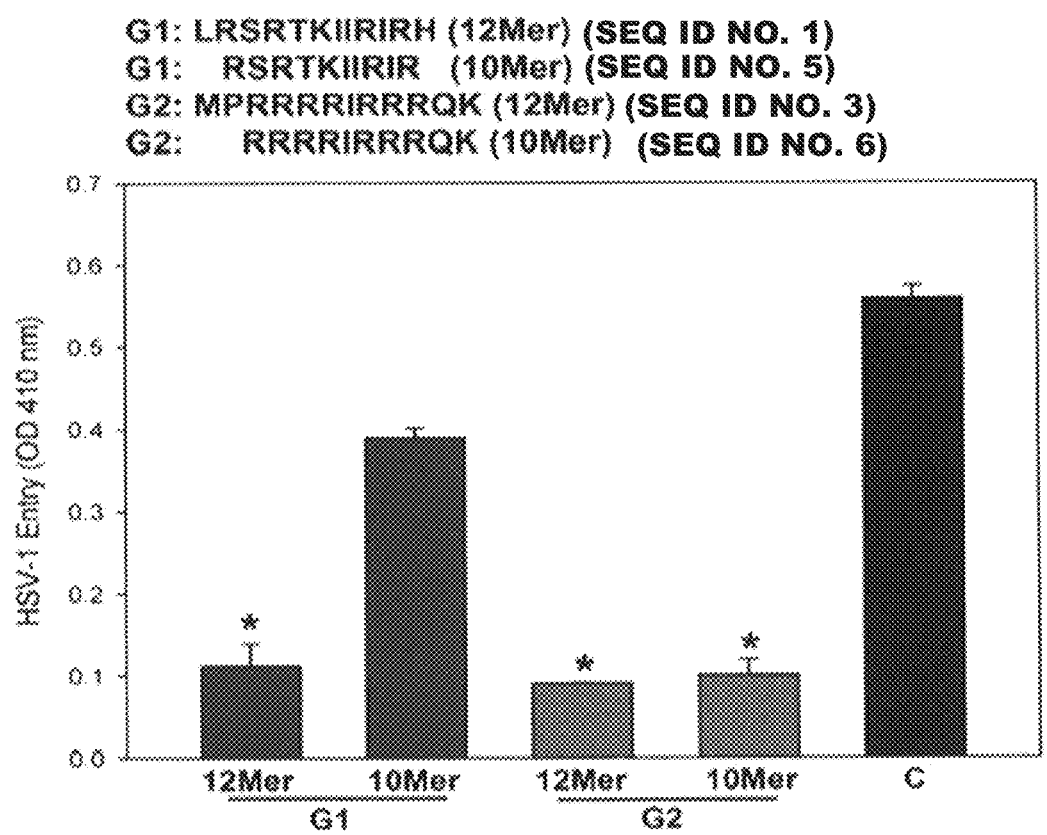
FIG. 4 presents the results of deletion analysis and alanine scanning mutagenesis, which reveal the significance of positively charged residues in HSV-1 entry inhibition.

As shown in FIG. 4A, the 10-mer version of G2 was very similar to the 12-mer in its ability to block HSV-1 entry into CF. In contrast, the 10-mer version of G1 peptide almost completely lost its ability to block HSV-1 entry into target cells. Thus, it is terminal L and H residues appear to be required for the anti-HSV-1 activity of G1. G2, on the other hand, relies more on its charged residues for its functional activity.

Alanine (A) scanning mutagenesis was performed to identify specific amino acid residues responsible for each peptide's function, stability, and conformation. O'Nuallain et al., Biochemistry 46:13049-13058 (2007). Twelve synthetic peptides were made whereby each residue of G2 was sequentially replaced with an alanine residue and corresponding changes in the G2 peptide were evaluated for their ability to affect viral entry (FIG. 4B). The location of alanine in the peptide is denoted by a number next to it. Cp represents the control peptide and the oligomeric G2 is listed as G2-O. FIG. 4B depicts the relative loss of inhibitory potential upon substitution of a residue within G2 by an alanine Activity of each peptide was normalized against the wild-type G2, which was kept at 1.00. Numbers higher than 1 show loss of activity whereas a lower number represents gain of activity.

This Example demonstrates that the first four arginine (R) residues and the last R and lysine (K) residue were essential. The middle two amino acids could be substituted with only a moderate loss of activity. The uncharged amino acids each tolerated substitution with alanine. Under similar experimental conditions, G2 oligomers (G2-O) were also examined and it was evident that they blocked infection about 2-fold better than G1 (FIG. 4B). These mutagenesis results demonstrate that the presence of positively charged amino acid residues plays an important role in HSV-1 entry blocking activity shown by G2.

Example 5

G2 Represents a Class of Broad Spectrum Anti-HS Peptides with Activity Against Multiple Herpesviruses This Example demonstrates that G2, but not G1, is effective in blocking viral entry of herpesvirus family members in addition to α-herpesviruses (e.g., HSV-1).

Many infectious viruses, including many herpesviruses, utilize cell surface HS moieties during viral binding and entry. Shukla and Spear, J. Clin. Invest. 108:503-510 (2001). As with HSV-1 (an α-herpesvirus), β-herpesvirus (cytomegalovirus; CMV) and γ-herpesvirus (human herpesvirus-8; HHV-8) also use HS during cell entry and fusion. Liu and Throp, Med. Res. Rev. 22:1-25 (2002) and Shukla and Spear, J. Clin. Invest. 108:503-510 (2001).

Figure 5:
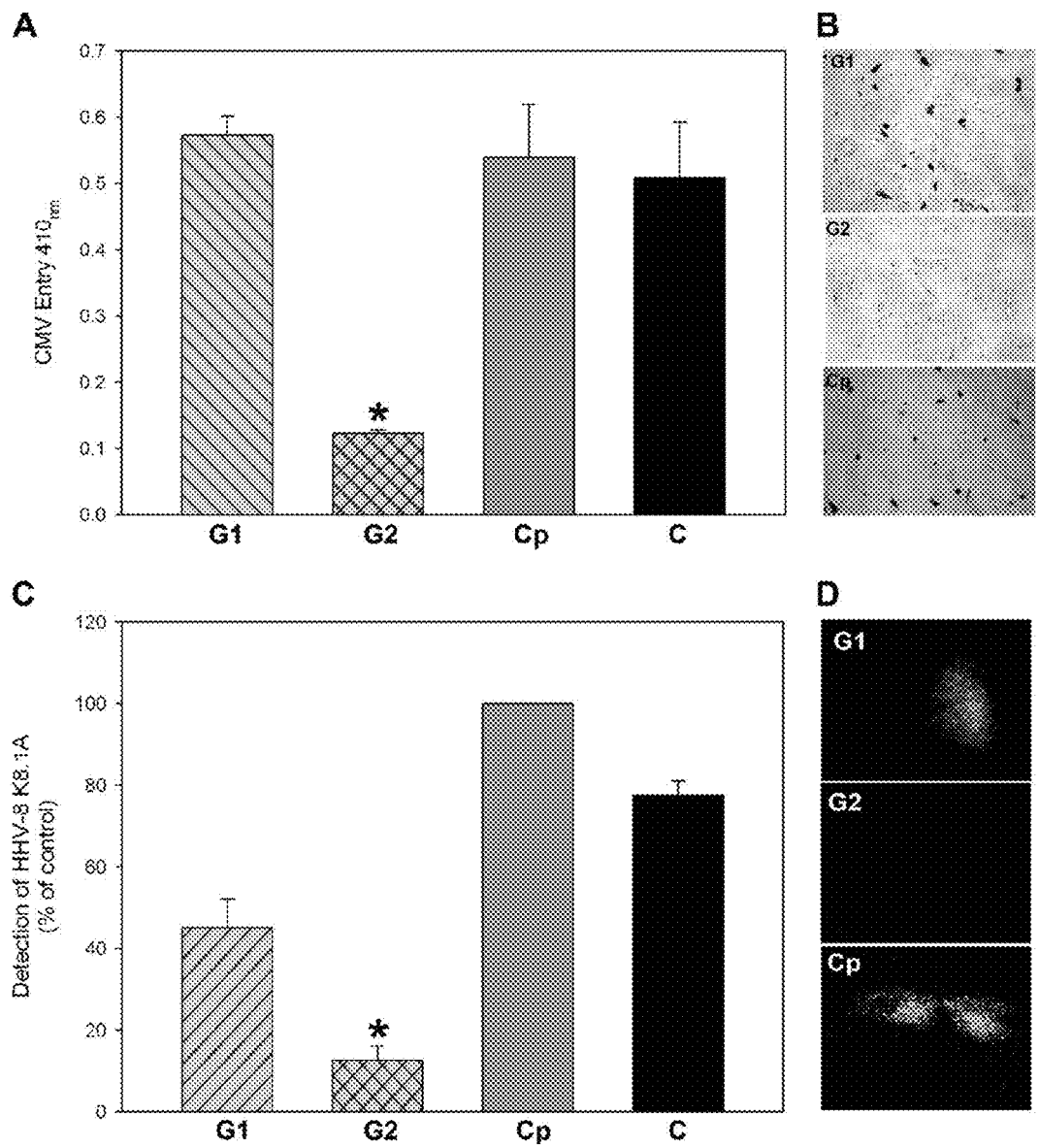
FIG. 5 demonstrates that G2 blocks cellular entry by representative members of beta and gamma herpesvirus subfamilies (CMV and HHV-8).

In order to detect each peptide's effect on viral entry, Lac Z-expressing reporter CMV and GFP-expressing HHV-8 viruses (Viera et al., J. Virol. 72:5182-5188 (2000)) and their natural target cells were employed for entry measurements. G2 peptide, but not G1 peptide, showed clear effects against CMV and HHV-8 (FIG. 5). A monolayer of cultured RPE cells grown in a 96 well plate were pre-treated with G1, G2, or control peptide (Cp) at 0.5 mM concentration (FIG. 5A). A mock-treated population of RPE cells served as positive control (abbreviated as C). After 60 min of incubation at room temperature, the cells were infected with β-galactosidase expressing CMV reporter virus. After 8 h, viral entry was measured as described for FIG. 1.

The effect of CMV entry blocking activity of G1, G2 or Cp peptide for individual RPE cells was determined by X-gal staining, which yields an insoluble blue product upon hydrolysis by β-galactosidase (FIG. 5B). Individual cells were examined using a Zeiss Axiovert 100 microscope at 20× magnification. Infected cells turn blue. These data demonstrate that G2 peptide was effective in blocking CMV entry into RPE cells, whereas G1 peptide had no effect on viral entry. The effect of G1 was similar to the control peptide (cp) or peptide untreated cells and the same pattern was repeated when the effects of the peptides were examined on a per cell basis by an X-gal assay.

The ability to block HHV-8 infection was examined in human conjunctival epithelial (HCjE) cells, a natural target for HHV-8 infection. Human conjunctival (HCjE) cells were pre-incubated with G1, G2 or control peptide (Cp) were infected with HHV-8 virions for 48 h at 37° C. After incubation the cells were washed thoroughly to remove unbound viruses. GFP-expression of HHV-8 was quantitated by determining relative fluorescence units (RFU) using a 96-well fluorescence reader (TECAN). Emission of fluorescence indicates virus infection. These data, which are presented in FIG. 5C, are the means of triplicate measures and are representative of 3 independent experiments. Compared to G1 or Cp treated cells, G2 treated HcjE cells had relatively low GFP-expression. This suggested that G2 was able to block infection. While G1 also demonstrated a reduction in fluorescence in the representative case shown in FIG. 5C, it was not found to be statistically significant upon repeated experiments. This was confirmed by examination of individual cells by fluorescence microscopy.

Viral replication in HCjE cells was visualized under fluorescent microscope (Zeiss Axiovert 100) in cells that were pretreated with G1, G2 or Cp, as described above (FIG. 5D). Asterisks indicate significant difference from controls and/or treatments ($P<0.05$, t test) and error bars represent SD. Cells treated with G2 did not show fluorescence originating from GFP virus replication. However, the fluorescence was more easily seen with G1 or Cp treated cells. The results suggest that G2 is more effective than G1 in blocking entry of divergent herpesviruses. G1 may have some activity but the virus can possibly overcome it easily.

Example 6

Mechanism for HSV-1 Entry Inhibition by the Peptides

This Example demonstrates that G2 peptide prevents target cell infection by herpesviruses by blocking viral HS binding sites and, hence, viral attachment.

Cultured CF were pre-incubated with 0.5 mM G2 peptide or control-peptide (cp) and then infected with a GFP-tagged HSV-1(K26GFP) virus. Cells were fixed at 60 min post-infection and stained for F-actin and the nucleus (DAPI).

GFP-expressing HSV-1(K26GFP) binding to CF in presence and absence of G2 peptides was examined by fluorescence microscopy (FIG. 6A). CF were grown in collagen coated chamber slides and incubated at room temperature for 60 min with G2 (+) or control Cp (G2 (−)) peptide. This was followed by the incubation of the cells in cold with GFP-expressing HSV-1(K26GFP) for 30 min and washing of unbound virioins with PBS. Cells were fixed, stained with phalloidin for F-actin and DAPI for nuclei and examined by a fluorescence microscope (Leica, SP2). The presence of the virus was shown by detecting GFP. These data demonstrated that G2-treated cells resisted virus attachment as compared to the control peptide treated cells.

To examine this effect on a population of $10^5$ cells, GFP intensity as an indicator of virus binding, was measured after incubation with the virus in cold and rigorous washing of the cells afterwards (FIG. 6B). Relative virus binding to CF was estimated by fluorescence measurements. Cultured CF were pre-incubated with G2 and control peptide (Cp) for 60-min before ice-cold incubation with GFP-expressing HSV-1 virus for 30 min. Cells were washed 3 times and viruses remaining on cell surfaces were assayed for GFP fluorescent intensity using a fluorescence reader (Tecan). Clearly, the binding was significantly higher in Cp-treated compared to G2 peptide treated cells.

GFP-expressing HSV-1(K26GFP) intensity as a surrogate for virus binding was quantified in presence G2 or control peptide (abbreviated as C) by flow cytometry (FIG. 6C). The cell/virus incubation was performed as described above. G2 peptides block HSV-1 replication into cultured human corneal fibroblasts (CF) (FIG. 6D). Cultured CF were pre-incubated with G2 or mock-treated (Cp) before infection with HSV-1(K26GFP) virus for 6 h. Viral replications in CF were quantified 0-36 h post-infection by measuring GFP fluorescent intensity using a fluorescence reader (Tecan). The data shown are the means of triplicate measures and are representative of three independent experiments. Asterisks indicate significant difference from other treatments (P<0.01, t test), error bars represent standard deviation (SD).

Example 7

G2 Peptide Acts by Inhibiting HSV-1 Binding to HS

This Example demonstrates, via flow cytometry detection, a significant reduction of GFP reporter virus binding to cells pretreated with G2.

Figure 6:
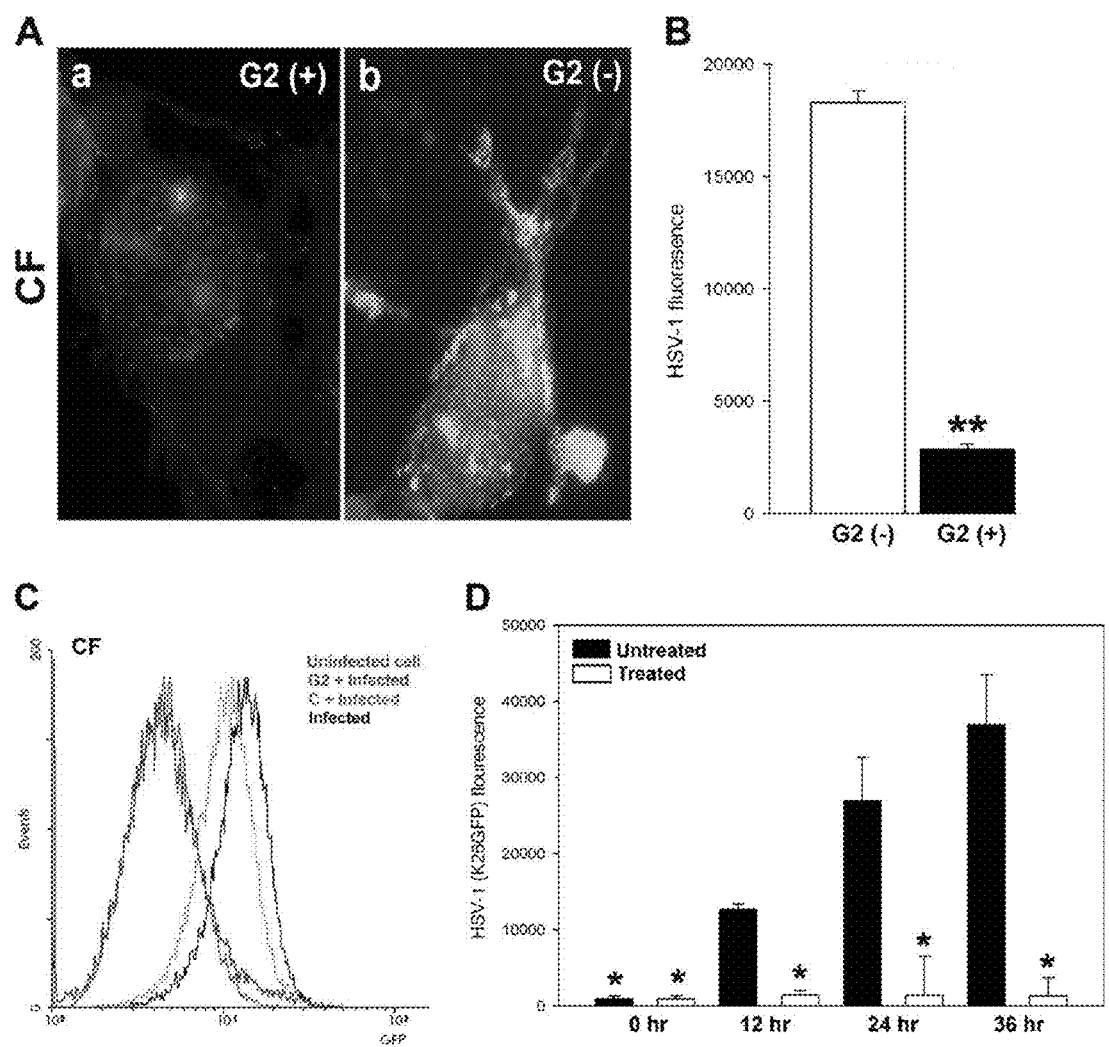
FIG. 6 demonstrates that G2 functions by preventing HSV-1 attachment to cells, which results in loss of binding and viral replication.

Primary cultures of human CF pretreated with G2 peptide or control peptide (C) were analyzed for HSV-1(K26GFP) binding. The peptide untreated CF incubated with the virus served as a positive control and uninfected CF served as a negative background control. The results presented in FIG. 6 demonstrate that the virus failed to bind G2 peptide treated CF (FIG. 6C). While the control peptide exhibited a low level inhibitory activity, the activity of the G2 peptide was far more robust. This result confirms that G2 has the ability to block virus attachment to cells.

To further confirm that blocking of viral attachment results in a reduction of viral replication, GFP fluorescence was measured as a function of time (K26GFP) (Desai and Person *J. Virol.* 72:7563-7568 (1998)) in both G2- and mock-treated cells. GFP intensity (which reflects the degree of virus production) increased significantly over time (FIG. 6D) in mock-treated cells but not when the cells were treated with G2. These results demonstrate that G2 blockage of virus binding results in a substantial reduction of viral replication.

Example 8

Pretreatment of G2 Peptide to the Target Cell Significantly Affects Cell-to-Cell Fusion and Viral Spread This Example demonstrates that G2 not only blocks viral attachment to a target cell, but it also inhibits viral penetration by blocking membrane fusion.

Since G2 was isolated against 3-OS HS, which can mediate viral penetration by promoting membrane fusion (Tiwari et al., *J. Gen. Virol.* 85:805-809 (2004)), the ability of G2 to block HSV-1 glycoprotein-mediated membrane fusion was tested. Pertel et al., *Virology* 279:313-324 (2001). The same membrane fusion is used during polykaryocytes formation and cell-to-cell spread. Tiwari et al., *FEBS Letters* 581:4468-4472 (2007) and Tiwari et al., *Biochemical and Biophysical Research Communications* 390:382-387 (2009). 3-OST-3 expressing CHO-K1 cells and primary cultures of human CF were pre-incubated with G2 peptide followed by co-culture with effector CHO-K1 cells expressing HSV-1 glycoproteins. The membrane fusion that ensues upon co-culturing the cells can be estimated by a Luciferase based reporter assay. Pertel et al., *Virology* 279:313-324 (2001). Likewise, polykaryocyte formation can be visualized by Giemsa staining.

Figure 7:
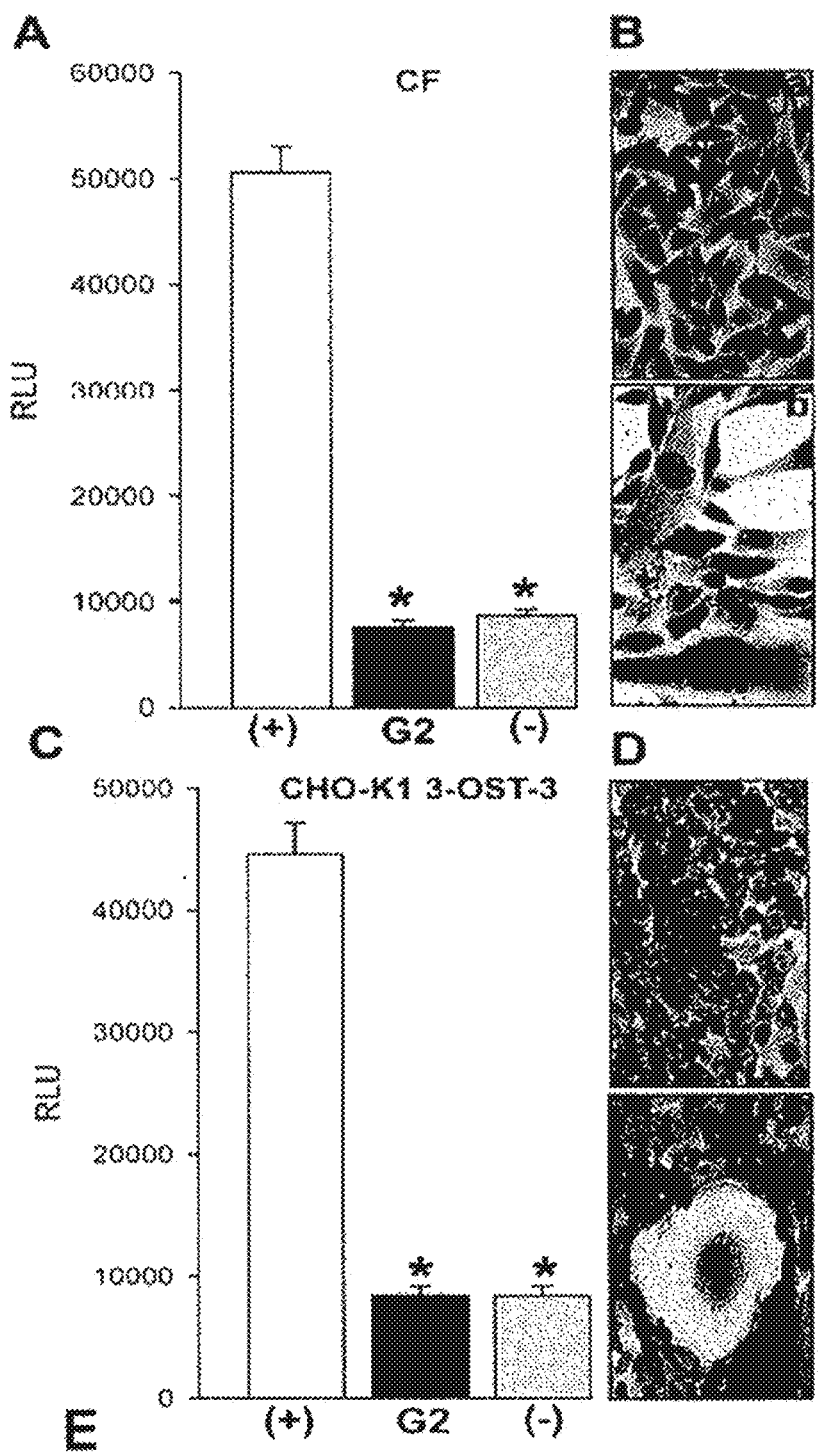
FIG. 7 demonstrates the activity of G2 against HSV-1 glycoprotein induced cell-to-cell fusion and spread.

FIG. 7 shows "effector" CHO-K1 cells expressing HSV-1 glycoproteins (gB, gD, gH-gL and T7 polymerase) that were pre-incubated with G2 peptide (black bar) or 1×PBS (white bar) (+) for 90 min. Control effector cells (T7 polymerase and gD, gH-gL only) (−) were also pre-incubated with G2 for the same duration. The effector cells were then mixed with primary cultures of human corneal fibroblasts (CF; FIGS. 7A and 7B) or 3-OST-3-expressing CHO-K1 cells (FIGS. 7C and 7D) transfected with Luciferase gene under T7 control. Membrane fusion as a surrogate for viral spread was detected by monitoring luciferase activity (FIGS. 7A and 7C). Relative luciferase units (RLUs) were determined using a Sirius luminometer (Berthold detection systems). Error bars represent standard deviations. *P<0.05, one way ANOVA. Microscopic images of Gimesa (Fluka) stained polykaryocytes show the preventative effect of G2's on cell fusion (FIGS. 7B and 7D). Shown are 40× magnified photographs of cells undergoing membrane fusion (Zeiss Axiovert 200).

These data show that prior treatment with G2 was very effective in blocking membrane fusion (FIGS. 7A and 7C) and that this ability translates into the loss of syncytia formation (FIGS. 7Ba and 7Da) compared to mock-treated cells (FIGS. 7Bb and 7Db).

Example 9

G1 and G2 Peptides Show Protective Effects Against HSV-1 Infection of the Mouse Cornea This Example demonstrates that anti-HS and anti-3OS HS peptides exhibit efficacy as anti-HSV prophylactic agents and that HS is an important co-receptor for an ocular HSV-1 infection in vivo.

The abilities of G1 and G2 peptides against HSV-1 infection was tested in a mouse cornea model. The cornea is known to express many gD receptors including 3OS HS.

Tiwari et al., *J. Virol.* 80:8970-8980 (2006) and Tiwari et al., *FEBS Letters* 581:4468-4472 (2007). The cornea is also an attractive target for HSV-1 infection leading to the development of herpetic stromal keratitis (HSK), a potential blinding disease common in developed countries including United States. Liesegang, *Cornea* 20:1-13 (2001).

Figure 8:
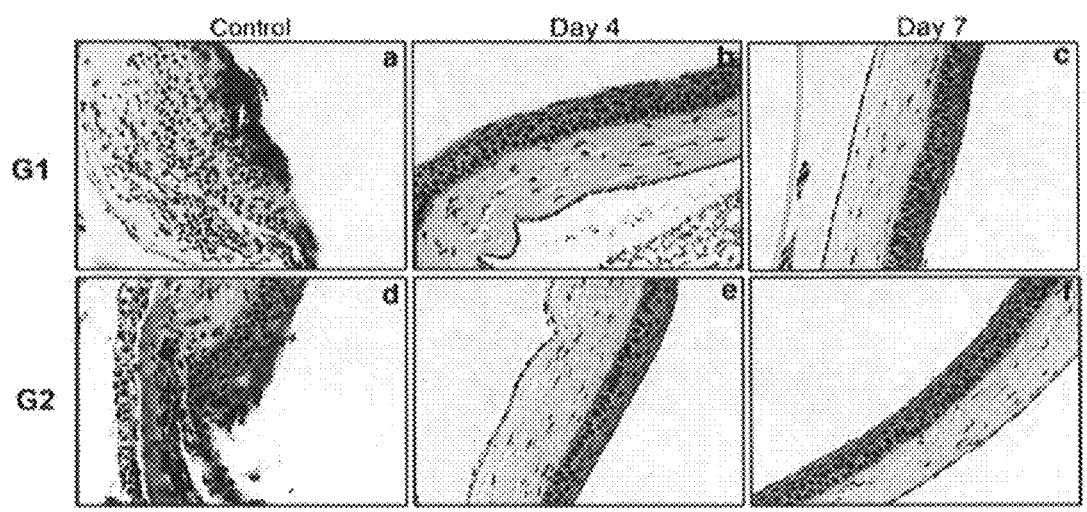
FIG. 8 demonstrates that G1 or G2 effectively block infection by HSV-1 in a mouse model of corneal keratitis.

Immunohistochemistry was used to locate HSV-1 glycoprotein D (gD) expression in the cornea pre-treated with either a control peptide, G1 or G2 followed by HSV-1 infection. 100 µl of G1, G2, or Cp (control) peptide at 0.5 mM concentration was poured into the mouse cornea as a prophylactic "eye drop" followed by an infection with HSV-1 (KOS) at $10^6$ PFU. At 4 or 7 days post infection, immunohistochemistry was performed using anti-HSV-1 gD polyclonal antibody. In sections of cornea of mice euthanized at $4^{th}$ and $7^{th}$ day following pretreatment with Cp-peptide (control) followed by virus inoculation, severe chronic inflammation combined with significant staining for HSV-1 gD was demonstrated on day 4 (FIG. 8A). HSV-1 staining was gone by day 7, which is typical with normal mice; however, damage to the corneal epithelium was still evident (FIG. 8B). In contrast, virtually no HSV-1 protein expression was detected in corneas treated with G1 or G2 peptide and the epithelium remained intact at both 4 and 7 days post infection (FIGS. 8B, 8C, 8E, and 8F).

Example 10

Synthesis and Characterization of riG1 and riG2 Peptides and Peptide Conjugates

Retro-inverso forms of inhibitory peptides (e.g., riG1 and riG2) may be tested and/or compared with corresponding wild-type peptides to assess efficacy, stability, or other characteristics. A variety of assays and testing methods may be used. Examples of suitable assays/methods may include, but are not limited to, the following methods/techniques, which can be used in isolation or in any suitable combination to compare or assess inhibitory peptides (e.g., Group 1 peptides and Group 2 peptides) and/or retro-inverso forms of such peptides.

In some embodiments, human corneal epithelial (HCE) cell or other suitable cell types may be used to assess inhibitory/therapeutic activity by retro-inverso peptides. The prophylactic potential of retro-inverso forms for inhibiting virus entry may be assessed by adding the retro-inverso forms to human corneal epithelial (HCE cells) before virus adsorption to the HCE cells. The therapeutic potential of retro-inverso forms may be assessed by adding the retro-inverso forms to the HCE cells after virus adsorption to the HCE cells. Virus entry may be tested before/after virus adsorption, and any reduction in cell entry and infection may be determined.

In some embodiments, a VP16 translocation assay may be used to assess virus entry deficiency. For example, confluent HCE cells may be exposed to a virus, incubated at 37° C. for one hour (entry period), and subsequently processed to detect VP16 by Western blotting.

In other embodiments, a plaque formation assay may be used to assess the ability of retro-inverso forms to interfere with cell-to-cell spread of a virus. For example, after HSV-1(17syn+) adsorption (under prophylactic or therapeutic treatment condition), HCE cells may be cultured in methylcellulose media to prevent free virus spread. At 36-48 h later, the plaques may be counted and the plaque sizes may be measured to assess cell-to-cell spread of the virus.

In still other embodiments, the ability of retro-inverso peptides to inactivate HSV-1 virions in solution may be tested by exposing virus to a retro-inverso peptide, and subsequently pelleting the virus to remove the peptide prior to infection. Reporter virus entry and plaque assays may be used to determine virus neutralization.

In various embodiments, retro-inverso peptides may be assessed to determine whether they have enhanced stability in comparison to the corresponding wild-type peptides. For example, cells may be pretreated with retro-inverso peptides, and the duration for which the pretreatment of cells induces resistance to infection may be measured. After exposing the cells to peptide (wild-type or ri-form), the cells may be infected with HSV-1(17) for 12, 24, 36, 48, and 72 h. Plaques may be counted thereafter.

These and/or other methods and techniques may be used to assess the prophylactic and therapeutic potential of retro-inverso forms of Group 1/2 peptides. In some embodiments, retro-inverso forms may offer better efficacy and/or stability than G1/G2 peptides.

Peptide Conjugates

In further studies aimed at improving the antiviral activity of the G1/G2, a C-terminal cysteine may be added as a coupling site for peptide dimerization by cysteine oxidation with dimethyl sulfoxide. HPLC chromatography may be performed to confirm dimer formation. The dimer may be tested by various methods, such as the methods described above, and compared with monomeric forms under anaerobic conditions. Such a dimer may be more effective, and may be at least 2-fold more effective, than the monomer. In some embodiments, a retro-inverso peptide and/or dimer as described herein may have efficacy in vitro against HSV-1 infection.

The efficacy of ACV, a replication blocking nucleoside analog, is well established. However, combining it with an entry blocking agent, such as G1, riG1, G2 and/or riG2 peptide, may provide better delivery of ACV or other such treatments to the nuclei, enhance efficacy, reduce non-specific cytotoxicity, and/or prevent development of resistance against ACV. Thus, the combination of ACV with an entry blocking agent such as G1, riG1, G2, or riG2 peptide may enhance the efficacy of the ACV by several fold. This ACV-peptide conjugate, or "super drug," may block virus entry, membrane fusion and virus replication, and/or render the virus virtually non-infectious and unable to spread from cell to cell. In some embodiments, an ACV-peptide conjugate, or "super drug" as described herein, may provide better therapeutic efficacy than either of the components of the ACV-peptide conjugate alone. In some embodiments, an ACV-peptide conjugate may include G2 or riG2 in combination with ACV (e.g., G2/ACV or riG2/ACV). The G2 or riG2 may block HSV-1 entry and cell-to-cell spread of the virions. In an uninfected/infected mixed cell population, about 400% more G2/ACV or riG2/ACV may be diverted to infected cells than to uninfected cells because infected cells express higher amounts of HS, to which G2 and riG2 bind. In some embodiments, G2 (riG2) may guide G2/ACV (riG2/ACV) conjugate to the nuclei where ACV will block viral replication ACV is a chain terminator for viral DNA synthesis. In an embodiment, ACV may be chemically coupled by esterification of ACV with a protected G2 peptide or riG2 peptide followed by acid promoted deprotection. ACV has been shown to be stable under peptide deprotection condition. The attachment of G2 or riG2 to ACV may significantly enhance the cellular uptake of ACV by infected cells, which express higher HS. Once inside the cells, the intracellular carboxyl esterases may cleave the ester linkage, releasing the ACV.

The efficacy of an ACV-blocking agent combination (e.g., ACV-G1, ACV-riG1, ACV-G2, or ACV-riG2) may be assessed and/or compared to that of other therapeutic agents (e.g., to ACV alone and blocking agent alone) by the methods described herein. In some embodiments, the efficacy of an ACV-blocking agent combination may be assessed by adding the therapeutic agents to be tested (e.g., G2, riG2, ACV, G2:ACV (1:1 mixture), riG2:ACV (1:1 mixture), G2-ACV, or riG2-ACV) to human corneal epithelial (HCE) cells either before (prophylactic) or after (therapeutic) virus adsorption to the HCE cells, and assessing/comparing loss or reduction of entry and infection among the experimental groups. The VP16 translocation assay may be used as described above to assess any entry deficiency of the virus resulting from the application of the therapeutic agents. The plaque formation assay may be used to assess the effect of the therapeutic agents on the ability of the virus to replicate. The ability of the virus to spread from infected cells to uninfected cells may be determined by mixing HCE cells infected with HSV-1 (MOI 0.1) for 2-6 h with uninfected cells and treating the mixed cells with the therapeutic agents. At 36 h later, a plaque assay may be performed. If peptide conjugation can uniquely target ACV to infected cells, a significant loss of plaque formation should be observed in the conjugate-treated cells. Such a result would indicate improved therapeutic efficacy compared to the other therapeutic agents/groups tested. Optionally, the efficacy of G2/ACV and riG2/ACV conjugates may be tested in a therapeutic model of HSV-1 infection of the murine cornea.

We have shown that G2 can block cell-to-cell fusion, a phenomenon that is required for virus spread. Therefore, G2 and riG2 peptides, which also block membrane fusion and entry, may demonstrate therapeutic efficacy against an existing primary and/or reactivated infection. Existing primary infections are slightly different from reactivated infections because a primary infection is caused by exposure to cell-free virions, whereas recurrent infections originate from cell associated virus returning to cause renewed symptoms. Therefore, G2 peptide, riG2 peptide, G2-ACV conjugate and riG2-ACV conjugate may be assessed for therapeutic efficacy in a primary infection model system, such as the system described below. As G1 does not appear to block membrane fusion, G1 may have lower efficacy in this therapeutic model.

To cause an existing primary infection, the corneas of mice may be treated topically with a saline solution containing 0.5 mM of G2, riG2 or control peptide starting at one day after corneal inoculation with HSV-1 McKrae ($10^4$ pfu/eye) strain. The peptide treatment may be continued daily for another four days. Animals may be monitored daily for change in body weight, genital inflammation, lesions, paralysis, and survival. Severely diseased mice may be sacrificed when moribund. A quantitative severity scale may be used for daily scoring of ocular lesion development, as described further below (e.g., 0=no disease, 1=slight erythema/swelling, 2=single or a few small lesions, 3=large or fused vesicles and 4=ulcerated lesions). Lesions may be monitored for up to 30 days. In order to obtain unbiased results, the observers may be masked from the identity of the treated and the placebo group. Groups of mice may be euthanized at 1, 2, 3, 4, 7, and 30 days following the first day of treatment, the left eyes, trigeminal ganglia (TG) and brain may be aseptically removed, and in some cases, the tissues may be flash frozen.

HSV-1 replication kinetics, HSV-1 gene expression and HSV-1 DNA levels may be determined in the eye and TG at 1, 2, 3, 4, 7, and 30 days after virus inoculation to evaluate the effectiveness of G2 and riG2 peptides on already-established HSV-1 keratitis, HSV spread from the eye to the TG, and establishment of latent infection in TG. Peptide-treated cells may demonstrate significantly less spread of the virus to the TG and hence, reduced latency. A similar set of experiments may be repeated with one or more other conjugates, such as G2-acylovir and riG2-ACV conjugates. Such conjugates may have greater efficacy than G2, riG2 or ACV alone.

Statistical Analysis:

Data can be assessed using independent samples T-test and repeated measures analysis of variance (ANOVA) followed by Scheffe's post hoc test. Differences between the means may be considered statistically significant if $P<0.05$. The results may be expressed as mean+/−standard deviation (SD) values.

What is claimed is:

1. A peptide comprising at least 10 consecutive amino acids of the sequence XXRRRRXRRRXK (SEQ ID NO: 4) or KXRRRXRRRRXX (SEQ ID NO: 10) wherein X is any amino acid, R is arginine, and K is lysine, wherein the peptide is no more than 12 amino acids long, and wherein at least one of the at least 10 amino acids is a D-amino acid.

2. The peptide of claim 1, wherein the peptide comprises the sequence XXRRRRXRRRXK (SEQ ID NO: 4) or KXRRRXRRRRXX (SEQ ID NO: 10).

3. The peptide of claim 1, wherein each X is independently selected from the group consisting of methionine, proline, isoleucine, and glutamine.

4. The peptide of claim 1, wherein the peptide comprises at least 10 consecutive amino acids of the sequence MPRRRRIRRRQK (SEQ ID NO: 3) or KQRRRIRRRRPM (SEQ ID NO: 9).

5. The peptide of claim 4, wherein the peptide comprises the sequence MPRRRRIRRRQK (SEQ ID NO: 3) or KQRRRIRRRRPM (SEQ ID NO: 9).

6. The peptide of claim 1, wherein the peptide is 12 amino acids in length.

7. The peptide of claim 1, wherein the peptide comprises 10 consecutive amino acids of the sequence RRRRIRRRQK (SEQ ID NO: 6) or KQRRRIRRRR (SEQ ID NO: 12).

8. The peptide of claim 1, wherein all the amino acids in the peptide are D-amino acids.

9. The peptide of claim 2, wherein all the amino acids in the peptide are D-amino acids.

10. The peptide of claim 3, wherein all the amino acids in the peptide are D-amino acids.

11. The peptide of claim 4, wherein all the amino acids in the peptide are D-amino acids.

12. The peptide of claim 5, wherein all the amino acids in the peptide are D-amino acids.

13. The peptide of claim 6, wherein all the amino acids in the peptide are D-amino acids.

14. The peptide of claim 7 wherein all the amino acids in the peptide are D-amino acids.

15. A method for blocking the binding of a virus to a target cell, the method comprising the step of contacting the target cell with the peptide of claim 1.

16. The method of claim 15, wherein the peptide comprises at least 10 consecutive amino acids of the sequence MPRRRRIRRRQK (SEQ ID NO: 3) or KQRRRIRRRRPM (SEQ ID NO: 9).

17. The method of claim 16, wherein the peptide comprises the sequence MPRRRRIRRRQK (SEQ ID NO: 3) or KQRRRIRRRRPM (SEQ ID NO: 9).

18. A peptide-therapeutic compound conjugate, comprising:
(a) a peptide comprising at least 10 consecutive amino acids of the sequence XXRRRRXRRRXK (SEQ ID NO: 4) or KXRRRXRRRRXX (SEQ ID NO: 10) wherein X is any amino acid, R is arginine, and K is lysine, wherein the peptide is no more than 12 amino acids long, and wherein at least one of the at least 10 amino acids is a D-amino acid; and
(b) a therapeutic compound; wherein the peptide is coupled to the therapeutic compound to generate the conjugate.

19. The peptide-therapeutic compound conjugate of claim 18, wherein the peptide comprises at least 10 consecutive amino acids of the sequence MPRRRRIRRRQK (SEQ ID NO: 3) or KQRRRIRRRRPM (SEQ ID NO: 9).

20. The peptide-therapeutic compound conjugate of claim 19, wherein the peptide comprises the sequence MPRRRRIRRRQK (SEQ ID NO: 3) or KQRRRIRRRRPM (SEQ ID NO: 9).

* * * * *

SEQUENCE LISTING

```
<160> NUMBER OF SEQ ID NOS: 12

<210> SEQ ID NO 1
<211> LENGTH: 12
<212> TYPE: PRT
<213> ORGANISM: Artificial Sequence
<220> FEATURE:
<223> OTHER INFORMATION: Synthetic construct

<400> SEQUENCE: 1

Leu Arg Ser Arg Thr Lys Ile Ile Arg Ile Arg His
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
```

```
<222> LOCATION: (1)..(1)
<223> OTHER INFORMATION: Xaa can be any amino acid
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (7)..(8)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be any amino acid
<220> FEATURE:
<221> NAME/KEY: MISC_FEATURE
<222> LOCATION: (12)..(12)
<223> OTHER INFORMATION: Xaa can be any amino acid

<400> SEQUENCE: 2

Xaa Arg Xaa Arg Xaa Lys Xaa Xaa Arg Xaa Arg Xaa
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic construct

<400> SEQUENCE: 3

Met Pro Arg Arg Arg Arg Ile Arg Arg Arg Gln Lys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (11)..(11)
<223> OTHER INFORMATION: Xaa can be any amino acid

<400> SEQUENCE: 4

Xaa Xaa Arg Arg Arg Arg Xaa Arg Arg Arg Xaa Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic construct

<400> SEQUENCE: 5
```

-continued

```
Arg Ser Arg Thr Lys Ile Ile Arg Ile Arg
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic construct

<400> SEQUENCE: 6

Arg Arg Arg Arg Ile Arg Arg Arg Gln Lys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic construct

<400> SEQUENCE: 7

His Arg Ile Arg Ile Ile Lys Thr Arg Ser Arg Leu
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be any amino acid
<220> FEATURE:
<221> NAME/KEY: MISC_FEATURE
<222> LOCATION: (12)..(12)
<223> OTHER INFORMATION: Xaa can be any amino acid

<400> SEQUENCE: 8

Xaa Arg Xaa Arg Xaa Xaa Lys Xaa Arg Xaa Arg Xaa
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic construct
```

```
<400> SEQUENCE: 9

Lys Gln Arg Arg Arg Ile Arg Arg Arg Met
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (11)..(11)
<223> OTHER INFORMATION: Xaa can be any amino acid
<220> FEATURE:
<221> NAME/KEY: MISC_FEATURE
<222> LOCATION: (12)..(12)
<223> OTHER INFORMATION: Xaa can be any amino acid

<400> SEQUENCE: 10

Lys Xaa Arg Arg Arg Xaa Arg Arg Arg Xaa Xaa
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic construct

<400> SEQUENCE: 11

Arg Ile Arg Ile Ile Lys Thr Arg Ser Arg
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic construct

<400> SEQUENCE: 12

Lys Gln Arg Arg Arg Ile Arg Arg Arg Arg
1               5                   10
```